United States Patent
Guillonneau et al.

(10) Patent No.: US 12,083,163 B2
(45) Date of Patent: Sep. 10, 2024

(54) ISOLATED INTERLEUKIN-34 POLYPEPTIDE FOR USE IN PREVENTING TRANSPLANT REJECTION AND TREATING AUTOIMMUNE DISEASES

(71) Applicants: INSERM (INSTITUT NATIONAL DE LA SANTÉ ET DE LA RECHERCHE MÉDICALE), Paris (FR); UNIVERSITÉ DE NANTES, Nantes (FR)

(72) Inventors: Carole Guillonneau, Nantes (FR); Ignacio Anegon, Nantes (FR); Séverine Bezie, Nantes (FR)

(73) Assignees: INSERM (INSTITUT NATIONAL DE LA SANTÉ ET DE LA RECHERCHE MÉDICALE), Paris (FR); UNIVERSITE DE NANTES, Nantes (FR)

( * ) Notice: Subject to any disclaimer, the term of this patent is extended or adjusted under 35 U.S.C. 154(b) by 306 days.

(21) Appl. No.: 17/371,646

(22) Filed: Jul. 9, 2021

(65) Prior Publication Data
US 2021/0401940 A1 Dec. 30, 2021

Related U.S. Application Data

(62) Division of application No. 16/174,837, filed on Oct. 30, 2018, now Pat. No. 11,090,362, which is a division of application No. 15/326,515, filed as application No. PCT/EP2015/066407 on Jul. 17, 2015, now Pat. No. 10,155,025.

(30) Foreign Application Priority Data

Jul. 17, 2014 (EP) .................................. 14306165
Jun. 16, 2015 (EP) .................................. 15305935

(51) Int. Cl.
| | |
|---|---|
| A61K 38/20 | (2006.01) |
| A61K 31/436 | (2006.01) |
| A61K 45/06 | (2006.01) |
| G01N 33/564 | (2006.01) |
| G01N 33/68 | (2006.01) |

(52) U.S. Cl.
CPC ............ A61K 38/20 (2013.01); A61K 31/436 (2013.01); A61K 45/06 (2013.01); G01N 33/564 (2013.01); G01N 33/6893 (2013.01); *G01N 2333/54* (2013.01); *G01N 2800/245* (2013.01); *G01N 2800/50* (2013.01)

(58) Field of Classification Search
CPC . A61K 38/20; G01N 33/6893; G01N 2333/54
See application file for complete search history.

(56) References Cited

U.S. PATENT DOCUMENTS

2012/0258075 A1 10/2012 Wyss-Coray

FOREIGN PATENT DOCUMENTS

| WO | 2010/149960 A1 | 12/2010 |
|---|---|---|
| WO | 2013/011021 A1 | 1/2013 |
| WO | 2013/156148 A1 | 10/2013 |
| WO | 2014/036357 A1 | 3/2014 |
| WO | 2015/025323 A1 | 2/2015 |

OTHER PUBLICATIONS

Mosteller and Wong, Drug Discovery Today, 19: 1212-1216, (2014).*
Baud'Huin et al: "Interleukin-34 is expressed by giant cell tumours of bone and plays a key role in RANKL-induced osteoclastogenesis", Journal of Pathology, vol. 221, pp. 77-86, Jan. 8, 2010.
Campbell et al: "The colony-stimulating factors and collagen-induced arthritis: exacerbation of disease by M-CSF and G-CSF and requirement for endogenous M-CSF", Journal of Leukocyte Biology, vol. 68, pp. 144-150, Jul. 2000.
Chemel et al: "Interleukin 34 expression is associated with synovitis severity in rheumatoid arthritis patients", Annals of Rhemuatoid Diseases, Oct. 28, 2012.
Chen et al: "The Critical Role of IL-34 in Osteoclastogenesis", PLOS One, vol. 6, issue 4, Apr. 8, 2011.
Chihara et al: "IL-34 and M-CSF share the receptor Fms but are not identical in biological activity and signal activation", Cell Death and Differentiation, vol. 17, pp. 1917-1927, May 21, 2010.
Doyle et al: "Effect of Recombinant Human Macrophage Colony-Stimulating Factor 1 on Immunopathology of Experimental Brucellosis in Mice", Infection and Immunity, vol. 60, No. 4, pp. 1465-1472, Apr. 1992.
Duluc et al: "Tumor-associated leukemia inhibitory factor and IL-6 skew monocyte differentiation into tumor-associated macrophage-like cells", Blood, vol. 110, issue 13, pp. 4319-4330, Dec. 15, 2007.
Eda et al: "Macrophage-colony stimulating factor and interleukin-34 induce chemokines in human whole blood", Cytokine, vol. 51, pp. 215-220, 2010.
Fancke et al: "M-CSF: a novel plasmacytoid and conventional dendritic cell poietin", Blood, vol. 11, No. 1, pp. 150-159, Jan. 1, 2008.
Foucher et al: "IL-34 Induces the Differentiation of Human Monocytes into Immunosuppressive Macrophages. Antagonistic Effects of GM-CSF and Ifnγ", PLOS One, vol. 8, issue 2, Feb. 2013.
Garceau et al: "Avian colony-stimulating factor 1 (CSF-1), interleukin-34 (IL-34), and CSF-1 receptor genes and gene products", Journal of Leukocyte Biology, vol. 87, pp. 753-764, May 2010.

(Continued)

*Primary Examiner* — Gyan Chandra
(74) *Attorney, Agent, or Firm* — WC&F IP

(57) ABSTRACT

The invention relates to an isolated interleukin-34 (IL-34) polypeptide for use in preventing or treating graft rejection, autoimmune disease, unwanted immune response against therapeutic proteins and allergy. The invention also provides an in vitro method for determining whether a patient is at risk of transplant rejection, autoimmune diseases, unwanted immune response against therapeutic proteins or allergies, comprising a step of determining the expression level of IL-34 in a biological sample obtained from said patient, wherein the presence of IL-34 is indicative of a reduced risk of transplant rejection, autoimmune diseases, unwanted immune response against therapeutic proteins or allergies.

11 Claims, 10 Drawing Sheets

Figure 1:
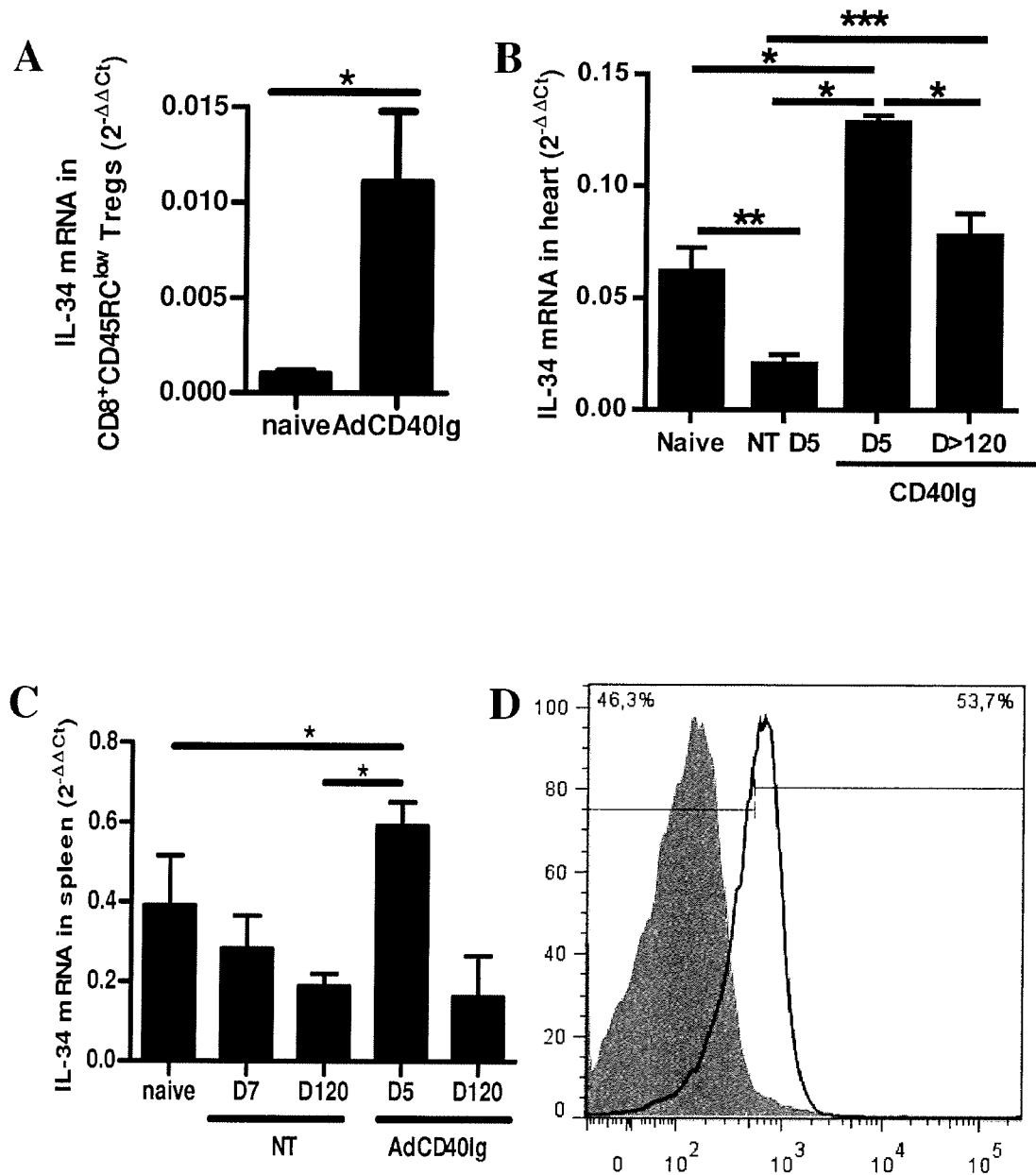

Specification includes a Sequence Listing.

(56) References Cited

OTHER PUBLICATIONS

Gilmore et al: "Inhibition of Day-I2 Spleen Colony-Forming Units by a Monoclonal Antibody to the Murine Macrophage/Monocyte Colony-Stimulating Factor Receptor", Blood, vol. 85, No. 10, pp. 2731-2734, May 1995.
Guilloneau et al: "CD40Ig treatment results in allograft acceptance mediated by CD8+CD45RClow T cells, IFN-γ, and indoleamine 2,3-dioxygenase", The Journal of Clinical Investigation, vol. 117, No. 4, pp. 1096-1106, 2007.
Guilloneau et al: "CD8+ regulatory T cells in solid organ transplantation", Current Opinion in Organ Transplantation, vol. 15, pp. 751-756, 2010.
Hamilton: "Colony-stimulating factors in inflammation and autoimmunity", Immunology, vol. 8, pp. 533-544, Jul. 2008.
Hashimoto et al: "Pretransplant CSF-1 therapy expands recipient macrophages and ameliorates GVHD after allogeneic hematopoietic cell transplantation", The Journal of Experimental Medicine, vol. 208, No. 5, pp. 1069-1082, May 2, 2011.
Holt et al: "MHC Class II Antigen-Bearing Dendritic Cells in Pulmonary Tissues of the Rat", The Journal of Experimental Medicine, vol. 167, pp. 262-274, Feb. 1998.
Jain et al: "Targeted drug delivery to macrophages", Expert Opinion On Drug Delivery, vol. 10, No. 3, pp. 353-367, vol. 10, No. 3, Jan. 6, 2013.
Jose et al: "Blockade of Macrophage Colony-Stimulating Factor Reduces Macrophage Proliferation and Accumulation in Renal Allograft Rejection", American Journal of Transplantation, vol. 3, pp. 294-300, 2003.
Kim et al: "Transplant tolerance: a new role for IL-34", The Journal of Clinical Investigation, vol. 125, No. 10, pp. 3751-3153, Oct. 2015.
Le Texier: "Immunoregulatory Function of IL-27 and TGF-β1 in Cardiac Allograft Transplantation", Transplantation, vol. 94, No. 3, pp. 226-233, Aug. 15, 2012.
Li et al: "Mechanization and Localization of CD8 Regulatory T Cells in a Heart Transplant Model of Tolerance", The Journal of Immunology, vol. 185, pp. 823-833, Jun. 11, 2010.
Li et al: "Rapamycin: One Drug, Many Effects", Cell Metabolism, vol. 19, pp. 373-379, Mar. 4, 2014.
Lin et al., "Discovery of a Cytokine and Its Receptor by Functional Screening of the Extracellular Proteome", Science, vol. 320, pp. 807-811, May 9, 2008.
Liu et al: "An instructive role of donor macrophages in mixed chimeras in the induction of recipient CD4+Foxp3+ Treg cells", Immunology and Cell Biology, vol. 89, pp. 827-835, Aug. 16, 2011.
Londono et al: "A Need for Biomarkers of Operational Tolerance in Liver and Kidney Transplantation", American Journal of Transplantation, Feb. 13, 2012.
Ma et al: "Structural Basis for the Dual Recognition of Helical Cytokines IL-34 and CSF-1 by CSF-1R", Structure, vol. 20, pp. 676-687, Apr. 4, 2012.

MacDonald et al: "The Colony-Stimulating Factor 1 Receptor is Expressed on Dendritic Cells during Differentiation and Regulates Their Expansion", The Journal of Immunology, vol. 175, pp. 1399-1405, 2005.
Menoret et al: "Phenotypic and Functional Characterization of CD8+ T Regulatory Cells", Methods in Molecular Biology, vol. 677, pp. 63-83, 2011.
Nandi et al: "Receptor-type Protein-tyrosine Phosphatase ζ is a Functional Receptor for Interleukin-34*", The Journal of Biological Chemistry, vol. 288, No. 30, pp. 21972-21986, Jul. 26, 2013.
Nankivell et al: "The Natural History of Chronic Allograft Nephropathy", The New England Journal of Medicine, vol. 349, No. 24, pp. 2326-2333, Dec. 11, 2003.
Niederkorn: "Emerging concepts in CD8+ T regulatory cells", Current Opinion in Immunology, vol. 20, pp. 327-331, 2008.
Picarda et al: "T-cell receptor specificity of CD8+ Tregs in allotransplantation", Immunotherapy, vol. 3, pp. 35-37, 2011.
Picarda et al: "MHC-derived allopeptide activates TCR-biased CD8+ Tregs and suppresses organ rejection", The Journal of Organ Investigation, vol. 124, No. 6, pp. 2497-2512, 2014.
Riquelme et al: "IFN-γ-induced iNOS Expression in Mouse Regulatory Macrophages Prolongs Allograft Survival in Fully Immunocompetent Recipients", Molecular Therapy, vol. 21, No. 2, pp. 409-422, Feb. 2013.
Sakurai et al: "Recombinant Human Macrophage-Colony Stimulating Factor Suppresses the Mouse Mixed Lymphocyte Reaction", Cellular Immunology, vol. 171, pp. 87-94, Apr. 12, 1996.
Sakurai et al., "Effect of Macrophage Colony-Stimulating Factor (M-CSF) on Mouse Immune Responses in Vivo", Immunopharmacology and Immunotoxicology, vol. 20, No. 1, pp. 79-102, Sep. 27, 2008.
Srinivas: "New agents, new ideas and new hope", Nature Review of Nephrology, vol. 8, pp. 74-75, Dec. 20, 2011.
Toromanoff et al: "Safety and Efficacy of Regional Intravenous (RI) Versus Intramuscular (IM) Delivery of rAAV1 and rAAV8 to Nonhuman Primate Skeletal Muscle", Molecular Therapy, vol. 16, No. 7, pp. 1291-1299, Jul. 2008.
Tzachanis et al: "Blockade of B7/CD28 in mixed lymphocyte reaction cultures results in the generation of alternatively activated macrophages, which suppress T-cell responses", Blood, vol. 99, No. 4, pp. 1465-1473, Feb. 15, 2002.
Van Rooijen et al: "Liposome mediated depletion of macrophages: mechanism of action, preparation of liposomes and applications", Journal of Immunological Methods, vol. 174, pp. 83-93, 1994.
Wang et al: "Interkeukin-34, a cytokine crucial for the differentiation and maintenance of tissue resident macrophages and Langerhans cells", European Journal of Immunology, vol. 44, pp. 1575-1581, 2014.
Wang et al: "IL-34 is a tissue-restricted ligand of CSF1R required for the development of Langerhans cells in microglia", Nature Immunology, vol. 13, No. 8, pp. 753-760, Aug. 2012.
Wei et al: "Functional overlap but differential expression of CSF-1 and IL-34 in the CSF-1 receptor-mediated regulation of myeloid cells", Journal of Leukocyte Biology, vol. 88, pp. 495-505, Sep. 2010.
Wood et al: "Regulatory immune cells in transplantation" Immunology, vol. 12, pp. 417-430, Jun. 2012.

* cited by examiner

A

B

A

B

US 12,083,163 B2

ISOLATED INTERLEUKIN-34 POLYPEPTIDE FOR USE IN PREVENTING TRANSPLANT REJECTION AND TREATING AUTOIMMUNE DISEASES

FIELD OF THE INVENTION

The invention is in the field of immunotherapy. More particularly, the invention relates to an isolated interleukin-34 (IL-34) polypeptide for use in preventing or treating transplant rejection, autoimmune disease, unwanted immune responses against proteins expressed in the course of gene therapy and/or therapeutic proteins (such as factor VIII, antibodies, etc) and allergy.

BACKGROUND OF THE INVENTION

Induction of immune tolerance is a powerful tool to control immune responses responsible for pathological situations. Cytokines, enzymes controlling metabolic pathways and cell surface molecules capable of inducing tolerance have been described. Despite these findings, evidence for other non-identified mechanisms exists and is thus important to identify new mediators of immune tolerance.

Organ transplantation has shown very significant improvements in both prevention and treatment of acute rejection but subclinical episodes and chronic graft dysfunction still heavily impact medium and long-term graft survival (1). Emerging therapeutic strategies, among them tolerance induction to donor antigens are moving into the clinics after years of experimental models work (2, 3). Among natural mechanisms and tolerance inductive strategies, different types of regulatory cells are among the most promising ones (4). $CD8^+$ regulatory T cells ($CD8^+$ Tregs) in the transplantation field but also in other pathophysiological situations have been highlighted in recent years (5-8). Cytokines, enzymes controlling metabolic pathways, and cell surface molecules, capable of inducing tolerance, have also been described as new mediators of immune tolerance.

A new cytokine called IL-34 was identified in 2008 (9). Studies showed that IL-34 shares homology with M-CSF and acts through a common receptor, CD115 also called CSF-1R (9) expressed on the cell surface of monocytes, and in the brain through a new described receptor, Receptor-type Protein-tyrosine Phosphatase ζ (PTP-ζ) (10). However, studies have demonstrated that IL-34 and M-CSF displayed distinct biological activity and signal activation (11), probably due to differential spatial and temporal IL-34 and M-CSF expression (12). IL-34 function has been mainly related until now with monocytes and macrophages (osteoclasts, microglia), as well as DCs, survival and function (12). Datas on the expression of IL-34 in resting cells were partially overlapping since mice with GFP under the control of the IL-34 promoter showed positive keratinocytes, hair follicles, neurons, proximal renal tubule cells and seminiferous tubule germ cells (12), whereas mRNA and protein analysis showed heart, brain, lung, liver, kidney, spleen, thymus, testicles, ovaries, prostate, colon, and small intestine, and abundant protein expression in spleen red pulp and osteoclast (9). Upon inflammation, other cells such as fibroblasts (13), osteoclasts (14) and articular synovial cells (13) upregulated IL-34 expression. So far, expression of IL-34 by other lymphoid cells and particularly T cells has not been described or demonstrated. Similarly, IL-34 has not been linked to effects on immune function of DCs or T cells since the decreased response to DTH antigens or CNS viral infections in IL-34-deficient mice was linked to paucity of Langerhan's and microglia, in skin and CNS respectively (12). Finally, there is no description to date of a role for IL-34 in tolerance in transplantation.

In a model of cardiac allograft in rats, it has been previously shown that blocking of CD40-CD40L, by CD40Ig treatment, induces long term graft survival through generation of of $CD8^{30}$ $CD45RC^{low}$ Tregs (termed $CD8^+$ CD40Ig Tregs) (15). It also been showed that these $CD8^+$ Tregs impose allogeneic tolerance partially through production of IFNγ and fibrinogen-like protein 2 (FGL2) (15, 16), and recognition of a dominant MHC-II-derived donor peptide (17). A potential role for FGL2 as an immune tolerogenic mechanism was first suspected when pan-genomic transcriptomic comparison of $CD8^+CD40Ig$ Tregs vs. $CD8^+$ $CD45RC^{low}$ Tregs from naïve rats showed increased FGL2 expression (16). The same transcriptomic analysis revealed that IL-34 was overexpressed in in $CD8^+CD40Ig$ Tregs from long-term recipients vs. $CD8^+CD45RC^{low}$ Tregs from naive animals.

Therefore, despite considerable advances in prevention of transplant rejection, such pathology remains associated with high morbidity and mortality and there is a desperate need for new mediators of immune tolerance and new tolerance inductive strategies (more particularly by down-regulating T-cell responses) for use in the prevention or the treatment of transplant rejection (or for use in the induction of transplant tolerance) as well as autoimmune disease, unwanted immune responses against proteins expressed in the course of gene therapy and/or therapeutic proteins and allergy.

Moreover, there is a need for an easily measurable biomarker predicting the risk of transplant rejection. Such a biomarker would thus be useful for monitoring transplanted patients and also adjusting their immunosuppressive treatment.

Until now, no study has examined whether IL-34 might induce immune tolerance and predict whether a transplanted patient is tolerant or not (displaying thus an increased risk of transplant rejection and therefore requiring an appropriate immunosuppressive treatment). Similarly, IL-34 has not been linked to effects on immune function of DCs or T cells and its suppressive potential in transplantation has never been suspected and studied.

SUMMARY OF THE INVENTION

In a first aspect, the invention relates to an isolated Interleukin-34 (IL-34) polypeptide or a polynucleotide encoding therefor for use in inducing immune tolerance in a patient in need thereof.

In a second aspect, the invention relates to an isolated IL-34 polypeptide or a polynucleotide encoding therefor for use in preventing or reducing transplant rejection in a patient in need thereof.

In a third aspect, the invention relates to an isolated IL-34 polypeptide or a polynucleotide encoding therefor for use in preventing or treating autoimmune diseases, unwanted immune response against therapeutic proteins and allergies in a patient in need thereof.

In a fourth aspect, the invention relates to pharmaceutical composition or a kit-of-part composition comprising an isolated IL-34 polypeptide or a polynucleotide encoding therefor and an immunosuppressive drug.

In a fifth aspect, the invention relates to an in vitro method for determining whether a patient is at risk of transplant rejection, autoimmune diseases, unwanted immune response against therapeutic proteins or allergies, comprising a step of determining the expression level of IL-34 in a biological sample obtained from said patient, wherein the presence of IL-34 is indicative of a reduced risk of transplant rejection, autoimmune diseases, unwanted immune response against therapeutic proteins or allergies.

In another aspect, the invention relates to method for adjusting the immunosuppressive treatment administered to a patient in need thereof, comprising the following steps of (i) performing the method for determining the risk as above defined, and (ii) adjusting the immunosuppressive treatment.

DETAILED DESCRIPTION OF THE INVENTION

The inventors demonstrated that IL-34 induces immunosuppression, inhibits primary T cell responses and induces T cell tolerance. This approach is of interest in the fields of autoimmunity, allergy, transplantation, treatment with therapeutic proteins and gene therapy, to avoid degradation of self or therapeutic molecules/tissues by the immune system.

The inventors demonstrated for the first time IL-34 involvement in CD8$^+$ Tregs immunosuppressive function in vitro. Blockade of its receptor CD115, expressed exclusively on myeloid cells, reverted IL-34 suppressive effect on effector CD4$^+$ T cells proliferation to pDCs, suggesting an indirect suppression of T cells response via pDCs. They showed for the first time that overexpression of IL-34 induces regulatory cells in vivo, capable of infectious tolerance. Accordingly, they identified IL-34 as a new mediator of the suppression by CD8$^+$ Tregs, and as a tolerogenic cytokine efficiently inhibiting allograft rejection.

The inventors also demonstrated that a combination comprising IL-34 and a suboptimal short-term immunosuppressive treatment (rapamycin) enables a synergistic increase of long-term graft survival vs. each treatment separately. They thus evaluated the immunoregulatory potential of this cytokine in transplantation using AAV-mediated overexpression and demonstrated a significant prolongation of allograft survival in association with a short 10-days course suboptimal dose of rapamycin, leading to 75% of indefinite survival, with total inhibition of alloantibody production.

The inventors further demonstrated that IL-34 is useful as biomarker for predicting the risk of transplant rejection.

Therapeutic Methods and Uses

The invention provides methods and compositions (such as pharmaceutical and kit-of part compositions) for use in inducing and/or maintaining immune tolerance in a patient in need thereof.

The invention also provides methods and compositions for use in preventing or reducing transplant rejection in a patient in need thereof.

The invention further provides methods and compositions for use in preventing or treating autoimmune diseases, alloimmune responses and allergies in a patient thereof.

In a first aspect, the invention relates to an isolated Interleukin-34 (IL-34) polypeptide for use in inducing and/or maintaining immune tolerance in a patient in need thereof.

The invention also relates to an isolated macrophage colony stimulating factor (M-CSF) polypeptide for use in inducing and/or maintaining immune tolerance in a patient in need thereof.

The invention also relates to a combination of an isolated IL-34 polypeptide and of an isolated M-CSF polypeptide for use in inducing and/or maintaining immune tolerance in a patient in need thereof.

As used herein, the term "immune tolerance" refers to a state of unresponsiveness of the immune system to substances or tissues that have the capacity to elicit an immune response.

As used herein, the term "immune response" includes T cell mediated and/or B cell mediated immune responses. Exemplary immune responses include T cell responses, e.g., cytokine production and cellular cytotoxicity, in addition, the term immune response includes immune responses that are indirectly effected by T cell activation, e.g., antibody production (humoral responses) and activation of cytokine responsive cells, e.g., macrophages Immune cells involved in the immune response include lymphocytes, such as B cells and T cells (CD4$^+$, CD8$^+$, Th1 and Th2 cells); antigen presenting cells (e.g. professional antigen presenting cells such as dendritic cells); natural killer cells; myeloid cells, such as macrophages, eosinophils, mast cells, basophils, and granulocytes.

For instance, immune responses are involved in transplant rejection, as well as in the concomitant physiological result of such immune responses, such as for example, interstitial fibrosis, chronic graft arteriosclerosis, or vasculitis Immune responses are also involved in autoimmune diseases and the concomitant physiological result of such immune responses, including T cell-dependent infiltration and direct tissue injury, T cell-dependent recruitment and activation of macrophages and other effector cells, and T cell-dependent B cell responses leading to autoantibody production.

Thus, treated patients with an IL-34 polypeptide in comparison with untreated patients display the following physiological features: a) a decreased level of an immune response (specific or not) (thought to be mediated at least in part by antigen-specific effector CD4$^+$ T and CD8+ lymphocytes); b) a delay in the onset or progression of a immune response (specific or not); or c) a reduced risk of the onset or progression of an immune response (specific or not). As used herein, the term "specific" immune tolerance occurs when immune tolerance is preferentially invoked against certain antigens in comparison with others.

By "patient in need thereof" is meant an individual suffering from or susceptible of suffering from transplant rejection, an autoimmune diseases, alloimmune responses or allergies to be treated. The individuals to be treated in the frame of the invention are mammals, preferably human beings.

In one particular embodiment, the patient in need thereof is a patient undergoing transplantation.

In a second aspect, the invention relates to an isolated IL-34 polypeptide for use in preventing or reducing transplant rejection in a patient in need thereof.

The invention also relates to an isolated M-CSF polypeptide for use in preventing or reducing transplant rejection in a patient in need thereof.

The invention also relates to a combination of an isolated IL-34 polypeptide and of an isolated M-CSF polypeptide for use in preventing or reducing transplant rejection in a patient in need thereof.

As used herein, the term "preventing or reducing transplant rejection" is meant to encompass prevention or inhibition of immune transplant rejection, as well as delaying the onset or the progression of immune transplant rejection. The term is also meant to encompass prolonging survival of a transplant in a patient, or reversing failure of a transplant in a patient. Further, the term is meant to encompass ameliorating a symptom of an immune transplant rejection, including, for example, ameliorating an immunological complication associated with immune rejection, such as for example, interstitial fibrosis, chronic graft atherosclerosis, or vasculitis.

As used herein, the term "transplant rejection" encompasses both acute and chronic transplant rejection. "Acute rejection" is the rejection by the immune system of a tissue transplant recipient when the transplanted tissue is immunologically foreign. Acute rejection is characterized by infiltration of the transplant tissue by immune cells of the recipient, which carry out their effector function and destroy the transplant tissue. The onset of acute rejection is rapid and generally occurs in humans within a few weeks after transplant surgery. Generally, acute rejection can be inhibited or suppressed with immunosuppressive drugs such as rapamycin, cyclosporin, anti-CD40L monoclonal antibody and the like. "Chronic transplant rejection" generally occurs in humans within several months to years after engraftment, even in the presence of successful immunosuppression of acute rejection. Fibrosis is a common factor in chronic rejection of all types of organ transplants.

The term "transplantation" and variations thereof refers to the insertion of a transplant (also called graft) into a recipient, whether the transplantation is syngeneic (where the donor and recipient are genetically identical), allogeneic (where the donor and recipient are of different genetic origins but of the same species), or xenogeneic (where the donor and recipient are from different species). Thus, in a typical scenario, the host is human and the graft is an isograft, derived from a human of the same or different genetic origins. In another scenario, the graft is derived from a species different from that into which it is transplanted, including animals from phylogenically widely separated species, for example, a baboon heart being transplanted into a human host.

In one embodiment the donor of the transplant is a human. The donor of the transplant can be a living donor or a deceased donor, namely a cadaveric donor.

In one embodiment, the transplant is an organ, a tissue, or cells.

As used herein, the term "organ" refers to a solid vascularized organ that performs a specific function or group of functions within an organism. The term organ includes, but is not limited to, heart, lung, kidney, liver, pancreas, skin, uterus, bone, cartilage, small or large bowel, bladder, brain, breast, blood vessels, esophagus, fallopian tube, gallbladder, ovaries, pancreas, prostate, placenta, spinal cord, limb including upper and lower, spleen, stomach, testes, thymus, thyroid, trachea, ureter, urethra, uterus. As used herein, the term "tissue" refers to any type of tissue in human or animals, and includes, but is not limited to, vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue, ophthalmic tissue.

In a particular embodiment, the transplant rejection is cardiac allotransplant rejection.

As used herein, the term "cells" refers to a composition enriched for cells of interest, preferably a composition comprising at least 30%, preferably at least 50%, even more preferably at least 65% of said cells.

In certain embodiments the cells are selected from the group consisting of multipotent hematopoietic stem cells derived from bone marrow, peripheral blood, or umbilical cord blood; or pluripotent (i.e. embryonic stem cells (ES) or induced pluripotent stem cells (iPS)) or multipotent stem cell-derived differentiated cells of different cell lineages such as cardiomyocytes, beta-pancreatic cells, hepatocytes, neurons, etc.

In one embodiment, the cell composition is used for allogeneic hematopoietic stem cell transplantation (HSCT) and thus comprises multipotent hematopoietic stem cells, usually derived from bone marrow, peripheral blood, or umbilical cord blood.

HSCT can be curative for patients with leukemia and lymphomas. However, an important limitation of allogeneic HCT is the development of graft versus host disease (GVHD), which occurs in a severe form in about 30-50% of humans who receive this therapy.

Polypeptides of the invention are useful in preventing or reducing Graft-versus-Host-Disease (GvHD).

Accordingly, in one embodiment, the patient in need thereof is affected with a disease selected from the group consisting of acute myeloid leukemia (AML); acute lymphoid leukemia (ALL); chronic myeloid leukemia (CML); myelodysplasia syndrome (MDS)/myeloproliferative syndrome; lymphomas such as Hodgkin and non-Hodgkin lymphomas, chronic lymphatic leukemia (CLL) and multiple myeloma.

In a third aspect, the invention relates to an isolated IL-34 polypeptide for use in preventing or treating autoimmune diseases, unwanted immune responses against proteins expressed in the course of gene therapy or therapeutic proteins and allergies in a patient thereof.

The invention also relates to an isolated M-CSF polypeptide for use in preventing or treating autoimmune diseases, unwanted immune responses against proteins expressed in the course of gene therapy or therapeutic proteins and allergies in a patient thereof.

The invention also relates to a combination of an isolated IL-34 polypeptide and of an isolated M-CSF polypeptide for use in preventing or treating autoimmune diseases, unwanted immune responses against proteins expressed in the course of gene therapy or therapeutic proteins and allergies in a patient thereof.

As used herein, the terms "prevent", "preventing" and "prevention" refer to the administration of therapy to an individual who may ultimately manifest at least one symptom of a disease, disorder, or condition, but who has not yet done so, to reduce the chance that the individual will develop the symptom of the disease, disorder, or condition over a given period of time. Such a reduction may be reflected, for example, in a delayed onset of the at least one symptom of the disease, disorder, or condition in the patient.

As used herein, the terms "treat", "treating" or "treatment" refers to the administration of therapy to an individual in an attempt to reduce the frequency and/or severity of symptoms of a disease, defect, disorder, or adverse condition of a patient.

As used herein, the term "autoimmune disease" refers to a disease in which the immune system produces an immune response (for example, a B-cell or a T-cell response) against an antigen that is part of the normal host (that is an auto-antigen), with consequent injury to tissues. In an autoimmune disease, the immune system of the host fails to recognize a particular antigen as "self" and an immune reaction is mounted against the host's tissues expressing the antigen.

Exemplary autoimmune diseases affecting humans include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease and ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, acquired hemophilia, thrombotic thrombocytopenic purpura and the like.

As used herein, the term "unwanted immune response against a therapeutic protein" refers to any unwanted immune reaction directed to proteins expressed in the course of gene therapy, and/or therapeutic proteins, such as factor VIII (hemophilia A) and other coagulation factors, enzyme replacement therapies, monoclonal antibodies (e.g. natalizumab, rituximab, infliximab), polyclonal antibodies, enzymes or cytokines (e.g. IFN β).

For instance, this approach can indeed be applied to suppress an immune response, especially to prevent immune reactions to specific proteins when their expression is restored by gene therapy in individuals with corresponding genetic deficiencies. Thus, an isolated IL-34 polypeptide according to the invention may be used to prevent immune reactivity towards proteins normally absent in the patient due to mutations, while their reconstitution is achieved by gene therapy.

Moreover, protein therapy is an area of medical innovation that is becoming more widespread, and involves the application of proteins, such as enzymes, antibodies or cytokines, directly to patients as therapeutic products. One of the major hurdles in delivery of such medicaments involves the immune responses directed against the therapeutic protein themselves. Administration of protein-based therapeutics is often accompanied by administration of immune suppressants, which are used in order to facilitate a longer lifetime of the protein and therefore increased uptake of the protein into the cells and tissues of the organism. General immune suppressants can however be disadvantageous due to the unspecific nature of the immune suppression that is carried out, resulting in unwanted side effects in the patient. Therefore, this approach can be applied to suppress an immune response against therapeutic proteins and peptides, such as therapeutic antibodies, cytokines, enzymes or any other protein administered to a patient.

As used herein, the term "allergy" or "allergies" refers to a disorder (or improper reaction) of the immune system. Allergic reactions occur to normally harmless environmental substances known as allergens; these reactions are acquired, predictable, and rapid. Strictly, allergy is one of four forms of hypersensitivity and is called type I (or immediate) hypersensitivity. It is characterized by excessive activation of certain white blood cells called mast cells and basophils by a type of antibody known as IgE, resulting in an extreme inflammatory response. Common allergic reactions include eczema, hives, hay fever, asthma, food allergies, and reactions to the venom of stinging insects such as wasps and bees.

As used herein, the terms "Interleukin-34 polypeptide" or "IL-34 polypeptide" are well known in the art and refer to a cytokine that promotes the proliferation, survival and differentiation of monocytes and macrophages. The term includes naturally occurring IL-34 isoforms (e.g. Q6ZMJ4 and Q6ZMJ4-2 with and without a Q81), variants (e.g. variants rs8046424 and rs7206509) and modified forms thereof. The naturally occurring human IL-34 protein has an aminoacid sequence of 242 amino acids provided in the UniProt database under accession number Q6ZMJ4 and is shown as follows (SEQ ID NO: 1) or a polypeptide having a sequence at least 80%, 85%, 90%, 95%, 96%, 97%, 98% or 99% identical to the sequence SEQ ID NO: 1:

```
MPRGFTWLRYLGIFLGVALGNEPLEMWPLTQNEECTVTGFLRDKLQYRSR

LQYMKHYFPINYKISVPYEGVFRIANVTRLQRAQVSERELRYLWVLVSLS

ATESVQDVLLEGHPSWKYLQEVETLLLNVQQGLTDVEVSPKVESVLSLLN

APGPNLKLVRPKALLDNCFRVMELLYCSCCKQSSVLNWQDCEVPSPQSCS

PEPSLQYAATQLYPPPPWSPSSPPHSTGSVRPVRAQGEGLLP
```

As used herein, the terms "macrophage colony stimulating factor polypeptide" or "M-CSF polypeptide" (also known as CSF-1, for "colony stimulating factor 1 polypeptide") refer to any native or variant (whether native or synthetic) cytokine which controls the production, differentiation, and function of macrophages. The term includes naturally occurring M-CSF variants and modified forms thereof. Thus, three distinct variant M-CSF isoforms produced through alternative mRNA splicing have been described, respectively a M-CSF[alpha] variant which refers to a protein of 256 amino acids provided in the UniProt Uniparc database under accession number UPI0000D61F83, a M-CSF[beta] variant which refers to a protein of 554 amino acids provided in the GenPept database under accession number NP_000748.3 and is encoded by the nucleic acid sequence provided in the GenBank database under accession number NM_000757.5, and a M-CSF[gamma] variant which refers to a protein of 438 amino acids provided in the GenPept database under accession number NP_757349.1 and is encoded by the nucleic acid sequence provided in the GenBank database under accession number NM_172210.2.

In one embodiment, the M-CSF polypeptide is the human isoform M-CSF[alpha] of 256 amino acids provided in the UniProt/Uniparc database under accession number UPI0000D61F83 and is shown as follows (SEQ ID NO: 4) or a polypeptide having a sequence at least 80%, 85%, 90%, 95%, 96%, 97%, 98% or 99% identical to the sequence SEQ ID NO: 4:

```
MTAPGAAGRCPPTTWLGSLLLLVCLLASRSITEEVSEYCSHMIGSGHLQS

LQRLIDSQMETSCQITFEFVDQEQLKDPVCYLKKAFLLVQDIMEDTMRPR

DNTPNAIAIVQLQELSLRLKSCFTKDYEEHDKACVRTFYETPLQLLEKVK

NVFNETKNLLDKDWNIFSKNCNNSFAECSSQGHERQSEGSFSPQLQESVF

HLLVPSVILVLLAVGGLLFYRWRRRSHQEPQRADSPLEQPEGSPLTQDDR

QVELPV
```

In one embodiment, the M-CSF polypeptide is the human isoform M-CSF[beta] of 554 amino acids provided in the GenBank database under accession number NP_000748.3 and is shown as follows (SEQ ID NO: 5) or a polypeptide having a sequence at least 80%, 85%, 90%, 95%, 96%, 97%, 98% or 99% identical to the sequence SEQ ID NO: 5:

```
MTAPGAAGRCPPTTWLGSLLLLVCLLASRSITEEVSEYCSHMIGSGHLQS

LQRLIDSQMETSCQITFEFVDQEQLKDPVCYLKKAFLLVQDIMEDTMRPR

DNTPNAIAIVQLQELSLRLKSCFTKDYEEHDKACVRTFYETPLQLLEKVK
```

-continued

NVFNETKNLLDKDWNIFSKNCNNSFAECSSQDVVTKPDCNCLYPKAIPSS

DPASVSPHQPLAPSMAPVAGLTWEDSEGTEGSSLLPGEQPLHTVDPGSAK

QRPPRSTCQSFEPPETPVVKDSTIGGSPQPRPSVGAFNPGMEDILDSAMG

TNWVPEEASGEASEIPVPQGTELSPSRPGGGSMQTEPARPSNFLSASSPL

PASAKGQQPADVTGTALPRVGPVRPTGQDWNHTPQKTDHPSALLRDPPEP

GSPRISSLRPQGLSNPSTLSAQPQLSRSHSSGSVLPLGELEGRRSTRDRR

SPAEPEGGPASEGAARPLPRFNSVPLTDTGHERQSEGSSSPQLQESVFHL

LVPSVILVLLAVGGLLFYRWRRRSHQEPQRADSPLEQPEGSPLTQDDRQV

ELPV

In one embodiment, the M-CSF polypeptide is the human isoform M-CSF[gamma] of 438 amino acids provided in the GenBank database under accession number NP_757349.1_and is shown as follows (SEQ ID NO: 6) or a polypeptide having a sequence at least 80%, 85%, 90%, 95%, 96%, 97%, 98% or 99% identical to the sequence SEQ ID NO: 6:

MTAPGAAGRCPPTTWLGSLLLLVCLLASRSITEEVSEYCSHMIGSGHLQS

LQRLIDSQMETSCQITFEFVDQEQLKDPVCYLKKAFLLVQDIMEDTMRPR

DNTPNAIAIVQLQELSLRLKSCFTKDYEEHDKACVRTFYETPLQLLEKVK

NVFNETKNLLDKDWNIFSKNCNNSFAECSSQDVVTKPDCNCLYPKAIPSS

DPASVSPHQPLAPSMAPVAGLTWEDSEGTEGSSLLPGEQPLHTVDPGSAK

QRPPRSTCQSFEPPETPVVKDSTIGGSPQPRPSVGAFNPGMEDILDSAMG

TNWVPEEASGEASEIPVPQGTELSPSRPGGGSMQTEPARPSNFLSASSPL

PASAKGQQPADVTGHERQSEGSSSPQLQESVFHLLVPSVILVLLAVGGLL

FYRWRRRSHQEPQRADSPLEQPEGSPLTQDDRQVELPV

As used herein, the term "polypeptide" refers to a polymer of amino acid residues joined by peptide bonds, whether produced naturally or synthetically, having no specific length. Thus, peptides, oligopeptides and proteins are included in the definition of polypeptide and these terms are used interchangeably throughout the specification, as well as in the claims. The term polypeptide does not exclude post-translational modifications that include but are not limited to phosphorylation, acetylation, glycosylation and the like. The term also applies to amino acid polymers in which one or more amino acid residue is an artificial chemical mimetic of a corresponding naturally occurring amino acid, as well as to naturally occurring amino acid polymers and non-naturally occurring amino acid polymer.

By an "isolated" polypeptide, it is intended that the polypeptide is not present within a living organism, e.g. within human body. However, the isolated polypeptide may be part of a composition or a kit. The isolated polypeptide is preferably purified. Such polypeptide is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated polypeptide is by the appearance of a single band following SDS-polyacrylamide gel electrophoresis of the protein preparation and Coomassie Brilliant Blue staining of the gel.

The term "IL-34 polypeptide" is herein defined as including the naturally occurring human polypeptide IL-34 and naturally-occurring allelic variations of the polypeptide. Allelic variations are naturally-occurring base changes in the species population which may or may not result in an amino acid change in a polypeptide or protein. Additionally, the IL-34 polypeptides according to the invention not only encompass polypeptides comprising or consisting of full-length IL-34 and variants thereof, but also polypeptides consisting of fragments thereof, provided the fragments are biologically active. Additionally included in this definition are both recombinant and synthetic versions of the polypeptide IL-34, which may contain induced modifications in the polypeptide and DNA sequences thereof. Accordingly, the term IL-34 polypeptide intends to encompass the functional equivalents of the IL-34 polypeptide encoded by the sequence SEQ ID NO: 1.

The term "M-CSF polypeptide" is herein defined as including the naturally occurring human polypeptide M-CSF and naturally-occurring allelic variations of the polypeptide. Allelic variations are naturally-occurring base changes in the species population which may or may not result in an amino acid change in a polypeptide or protein. Additionally, the M-CSF polypeptides according to the invention not only encompass polypeptides comprising or consisting of full-length M-CSF and variants thereof, but also polypeptides consisting of fragments thereof, provided the fragments are biologically active. Additionally included in this definition are both recombinant and synthetic versions of the polypeptide M-CSF, which may contain induced modifications in the polypeptide and DNA sequences thereof. Accordingly, the term M-CSF polypeptide intends to encompass the functional equivalents of the M-CSF polypeptides encoded by the sequence SEQ ID NO: 4, SEQ ID NO: 5 or SEQ ID NO: 6.

As used herein, a "functional equivalent" refers to a molecule (e.g. a recombinant polypeptide) that retains the biological activity and the specificity of the parent polypeptide. Therefore, the term "functional equivalent of the IL-34 polypeptide" includes variants and fragments of the polypeptide to which it refers (i.e. the IL-34 polypeptide) provided that the functional equivalents exhibit at least one, preferably all, of the biological activities of the reference polypeptide, as described below. Functional equivalents of the IL-34 polypeptide have been previously described (40). The term "functional equivalent of the M-CSF polypeptide" includes variants and fragments of the polypeptide to which it refers (i.e. the M-CSF polypeptide) provided that the functional equivalents exhibit at least one, preferably all, of the biological activities of the reference polypeptide, as described below.

A polypeptide "variant" refers to a biologically active polypeptide having at least about 80% amino acid sequence identity with the native sequence polypeptide. Such variants include, for instance, polypeptides wherein one or more amino acid residues are added, or deleted, at the N-or C-terminus of the polypeptide. Ordinarily, a variant will have at least about 80% amino acid sequence identity, more preferably at least about 90% amino acid sequence identity, and even more preferably at least about 95% amino acid sequence identity with the native sequence polypeptide.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid.

In the frame of the application, the percentage of identity is calculated using a global alignment (i.e., the two sequences are compared over their entire length). Methods for comparing the identity and homology of two or more sequences are well known in the art. The "needle" program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

Polypeptides consisting of an amino acid sequence "at least 80%, 85%, 90%, 95%, 96%, 97%, 98% or 99% identical" to a reference sequence may comprise mutations such as deletions, insertions and/or substitutions compared to the reference sequence. The polypeptide consisting of an amino acid sequence at least 80%, 85%, 90%, 95%, 96%, 97%, 98% or 99% identical to a reference sequence may correspond to an allelic variant of the reference sequence. It may for example only comprise substitutions compared to the reference sequence. The substitutions preferably correspond to conservative substitutions as indicated in the table below.

| Conservative substitutions | Type of Amino Acid |
| --- | --- |
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

As used herein polypeptide, a "fragment" refers to a biologically active polypeptide that is shorter than a reference polypeptide (i.e. a fragment of the IL-34 polypeptide or a fragment of the M-CSF polypeptide). Thus, the polypeptide according to the invention encompasses polypeptides comprising or consisting of fragments of IL-34 or M-CSF, provided the fragments are biologically active.

In the frame of the invention, the biologically active fragment may for example comprise at least 175, 200, 205, 210, 215, 220, 225, 230, 235, 240 consecutive amino acids of the IL-34 polypeptide.

In the frame of the invention, the biologically active fragment may for example comprise at least 150, 175, 200, 225, 250, 275, 300, 325, 350, 375, 400, 425, 450, 475, 500, 525 or 550 consecutive amino acids of the M-CSF polypeptide.

In one particular embodiment, the M-CSF polypeptide comprises or consists of a 150 amino acid polypeptide of human M-CSF and is shown as follows (SEQ ID NO: 7):

MTAPGAAGRCPPTTWLGSLLLLVCLLASRSITEEVSEYCSHMIGSGHLQS

LQRLIDSQMETSCQITFEFVDQEQLKDPVCYLKKAFLLVQDIMEDTMRPR

DNTPNAIAIVQLQELSLRLKSCFTKDYEEHDKACVRTFYETPLQLLEKVK

By "biological activity" of IL-34 or a functional equivalent thereof or M-CSF or a functional equivalent thereof is meant:

(i) the capacity to induce and/or maintain (at least 120 days in rat) immune tolerance (as described in the Section Examples; i.e. the capacity to inhibit the CD4+ and CD8+ T cell proliferation in a mixed lymphocyte reaction (MLR); and/or (ii) the capacity to prevent the transplant rejection in a model of organ allotransplantation (model of cardiac allotransplantation).

The skilled in the art can easily determine whether a functional equivalent of the IL-34 polypeptide or a functional equivalent of the M-CSF polypeptide is biologically active. To check whether the newly generated polypeptides inhibit the CD4+ T cell proliferation in a MLR and/or prevent the transplant rejection in a model of organ allotransplantation, a FACS analysis or a single cell gene expression profiling (see in Example section) may be performed for each polypeptide. Moreover, to check whether the newly generated polypeptides prevent the transplant rejection, a model of organ allotransplantation may be used (see in Example section). Additionally, a time-course and a dose-response performed in vitro or in vivo (e.g. by using a model of organ allotransplantation) will determine the optimal conditions for each polypeptide.

In one embodiment, the polypeptides of the invention may comprise a tag. A tag is an epitope-containing sequence which can be useful for the purification of the polypeptides. It is attached to by a variety of techniques such as affinity chromatography, for the localization of said polypeptide within a cell or a tissue sample using immunolabeling techniques, the detection of said polypeptide by immunoblotting etc. Examples of tags commonly employed in the art are the GST (glutathion-S-transferase)-tag, the FLAG™-tag, the Strep-tag™, V5 tag, myc tag, His tag (which typically consists of six histidine residues), etc.

In another embodiment, the polypeptides of the invention may comprise chemical modifications improving their stability and/or their biodisponibility. Such chemical modifications aim at obtaining polypeptides with increased protection of the polypeptides against enzymatic degradation in vivo, and/or increased capacity to cross membrane barriers, thus increasing its half-life and maintaining or improving its biological activity. Any chemical modification known in the art can be employed according to the present invention. Such chemical modifications include but are not limited to:

replacement(s) of an amino acid with a modified and/or unusual amino acid, e.g. a replacement of an amino acid with an unusual amino acid like Nle, Nva or Orn; and/or modifications to the N-terminal and/or C-terminal ends of the peptides such as e.g. N-terminal acylation (preferably acetylation) or desamination, or modification of the C-terminal carboxyl group into an amide or an alcohol group;

modifications at the amide bond between two amino acids: acylation (preferably acetylation) or alkylation (preferably methylation) at the nitrogen atom or the alpha carbon of the amide bond linking two amino acids;

modifications at the alpha carbon of the amide bond linking two amino acids such as e.g. acylation (preferably acetylation) or alkylation (preferably methylation) at the alpha carbon of the amide bond linking two amino acids.

chirality changes such as e.g. replacement of one or more naturally occurring amino acids (L enantiomer) with the corresponding D-enantiomers;

retro-inversions in which one or more naturally-occurring amino acids (L-enantiomer) are replaced with the corresponding D-enantiomers, together with an inversion of the amino acid chain (from the C-terminal end to the N-terminal end);

azapeptides, in which one or more alpha carbons are replaced with nitrogen atoms; and/or betapeptides, in which the amino group of one or more amino acid is bonded to the β carbon rather than the α carbon.

Another strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 60 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes. Such linkers may be used in modifying the polypeptides described herein for therapeutic delivery.

In still another embodiment, the polypeptides of the invention may be fused to a heterologous polypeptide (i.e. polypeptide derived from an unrelated protein, for example, from an immunoglobulin protein).

As used herein, the terms "fused" and "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. For instance, a recombinant fusion protein may be a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence.

As used herein, the term "IL-34 fusion protein" refers to a polypeptide comprising the IL-34 polypeptide or a functional equivalent thereof fused to heterologous polypeptide. The IL-34 fusion protein will generally share at least one biological property in common with the IL-34 polypeptide (as described above).

An example of an IL-34 fusion protein is an IL-34 immunoadhesin.

As used herein, the term "M-CSF fusion protein" refers to a polypeptide comprising the M-CSF polypeptide or a functional equivalent thereof fused to heterologous polypeptide. The M-CSF fusion protein will generally share at least one biological property in common with the M-CSF polypeptide (as described above).

An example of a M-CSF fusion protein is a M-CSF immunoadhesin.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The immunoglobulin sequence preferably, but not necessarily, is an immunoglobulin constant domain (Fc region) Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use. In one embodiment, the Fc region is a native sequence Fc region. In another embodiment, the Fc region is a variant Fc region. In still another embodiment, the Fc region is a functional Fc region. The IL-34 sequence portion and the immunoglobulin sequence portion of the IL-34 immunoadhesin may be linked by a minimal linker. The immunoglobulin sequence preferably, but not necessarily, is an immunoglobulin constant domain. The immunoglobulin moiety in the chimeras of the present invention may be obtained from IgG1, IgG2, IgG3 or IgG4 subtypes, IgA, IgE, IgD or IgM, but preferably IgG1 or IgG3.

As used herein, the term "Fc region" is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof.

Another example of an IL-34 fusion protein or M-CSF fusion protein is a fusion of the IL-34 polypeptide or of the M-CSF polypeptide with human serum albumin-binding domain antibodies (AlbudAbs) according to the AlbudAb™ Technology Platform as described in Konterman et al. 2012 AlbudAb™ Technology Platform—Versatile Albumin Binding Domains for the Development of Therapeutics with Tunable Half-Lives.

In another embodiment, the polypeptides of the invention may be combined/formulated with a drug delivery system suitable for therapeutic proteins.

Examples of such drug delivery system that may be used include various micro- as well as nanocarriers like microspheres/microparticles, liposomes, nanoparticles, dendrimers, niosomes and carbon nanotubes for targeted delivery of therapeutic proteins. In a particular embodiment, such drug delivery system is a drug delivery system suitable for cell-mediated drug delivery, in particular monocytes- and/or macrophages-mediated drug delivery as disclosed in Jain et al., 2013 (42).

Alternatively, the polypeptides of the invention may be encapsulated in red blood cells or erythrocytes. Various methods have been described to allow the incorporation of active ingredients into red blood cells including the method described in application EP 1 773 452 which is the method currently offering the best performance and has the advantage of being reproducible and of improving the encapsulation yield of active ingredient.

The polypeptides of the invention may be produced by any suitable means, as will be apparent to those of skill in the art. In order to produce sufficient amounts of IL-34 or M-CSF polypeptides for use in accordance with the invention, expression may conveniently be achieved by culturing under appropriate conditions recombinant host cells containing the polypeptide of the invention. Preferably, the polypeptide is produced by recombinant means, by expression from an encoding nucleic acid molecule. Systems for cloning and expression of a polypeptide in a variety of different host cells are well known.

When expressed in recombinant form, the polypeptide is preferably generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells. HeLa cells, baby hamster kidney cells and many others. Bacteria are also preferred hosts for the production of recombinant protein, due to the ease with which bacteria may be manipulated and grown. A common, preferred bacterial host is *E coli*.

Moreover, it should be noted that the majority of protein-based biopharmaceuticals bare some form of post-translational modification which can profoundly affect protein properties relevant to their therapeutic application. Protein glycosylation represents the most common modification (about 50% of human proteins are glycosylated). Glycosylation can introduce considerable heterogeneity into a protein composition through the generation of different glycan structures on the proteins within the composition. Such glycan structures are made by the action of diverse enzymes of the glycosylation machinery as the glycoprotein transits the Endoplasmatic Reticulum (ER) and the Golgi-Complex (glycosylation cascade). The nature of the glycan structure(s) of a protein has impact on the protein's folding, stability, life time, trafficking, pharmaco-dynamics, pharmacokinetics and immunogenicity. The glycan structure has great impact on the protein's primary functional activity. Glycosylation can affect local protein structure and may help to direct the folding of the polypeptide chain. One important kind of glycan structures are the so called N-glycans. They are generated by covalent linkage of an oligosaccharide to the amino (N)-group of asparagin residues in the consensus sequence NXS/T of the nascent polypeptide chain. N-glycans may further participate in the sorting or directing of a protein to its final target: the N-glycan of an antibody, for example, may interact with complement components. N-glycans also serve to stabilize a glycoprotein, for example, by enhancing its solubility, shielding hydrophobic patches on its surface, protecting from proteolysis, and directing intra-chain stabilizing interactions. Glycosylation may regulate protein half-life, for example, in humans the presence of terminal sialic acids in N-glycans may increase the half-life of proteins, circulating in the blood stream.

As used herein, the term "glycoprotein" refers to any protein having one or more N-glycans attached thereto. Thus, the term refers both to proteins that are generally recognized in the art as a glycoprotein and to proteins which have been genetically engineered to contain one or more N-linked glycosylation sites. As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs co-translationally in the lumen of the ER and continues post-translationally in the Golgi apparatus for N-linked glycoproteins.

A number of yeasts, for example, *Pichia pastoris, Yarrowia lipolytica* and *Saccharomyces cerevisiae* are recently under development to use the advantages of such systems but to eliminate the disadvantages in respect to glycosylation. Several strains are under genetical development to produce defined, human-like glycan structures on a protein. Methods for genetically engineering yeast to produce human-like N-glycans are described in U.S. Pat. Nos. 7,029,872 and 7,449,308 along with methods described in U.S. Published Application Nos. 20040230042, 20050208617, 20040171826, 20050208617, and 20060286637. These methods have been used to construct recombinant yeast that can produce therapeutic glycoproteins that have predominantly human-like complex or hybrid N-glycans thereon instead of yeast type N-glycans. As previously described, human-like glycosylation is primarily characterized by "complex" N-glycan structures containing N-acetylglusosamine, galactose, fucose and/or N-acetylneuraminic acid. Thus, several strains of yeasts have been genetically engineered to produce glycoproteins comprising one or more human-like complex or human-like hybrid N-glycans such as GlcNAcMan3GlcNAc2.

Alternatively, a nucleic acid encoding a polypeptide of the invention (such as the IL-34 polypeptide as shown in SEQ ID NO: 1 or the M-CSF polypeptide as shown in SEQ ID NO: 4, 5, 6 and 7) or a vector comprising such nucleic acid or a host cell comprising such vector may be used.

Accordingly, another aspect of the invention relates to a nucleic acid encoding an amino acid sequence comprising SEQ ID NO: 1 or SEQ ID NO: 4, 5, 6 and 7 as described here above, or a vector comprising such nucleic acid or a host cell comprising such vector, for use in inducing and/or maintaining immune tolerance in a patient in need thereof.

Another aspect of the invention relates to a nucleic acid encoding an amino acid sequence comprising SEQ ID NO: 1 or SEQ ID NO: 4, 5, 6 and 7 as described here above, or a vector comprising such nucleic acid or a host cell comprising such vector, for use in preventing or reducing transplant rejection in a patient in need thereof.

Still another aspect of the invention relates to a nucleic acid encoding an amino acid sequence comprising SEQ ID NO: 1 or SEQ ID NO: 4, 5, 6 and 7 as described here above, or a vector comprising such nucleic acid or a host cell comprising such vector, for use in preventing or treating autoimmune diseases, alloimmune responses and allergies in a patient thereof.

Nucleic acids of the invention may be produced by any technique known per se in the art, such as, without limitation, any chemical, biological, genetic or enzymatic technique, either alone or in combination(s).

In its broadest sense, a "vector" is any vehicle capable of facilitating the transfer of a nucleic acid to the cells. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the nucleic acid sequences of interest. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W. H. Freeman C.O., New York, 1990) and in MURRY ("Methods in Molecular Biology," vol.7, Humana Press, Inc., Cliffton, N.J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers and microencapsulation.

According to the invention, examples of host cells that may be used are human monocytes or macrophages (particularly those obtained from the subject to be treated).

The means by which the vector carrying the gene may be introduced into the cells include, but are not limited to, microinjection, electroporation, transduction, or transfection using DEAE-dextran, lipofection, calcium phosphate or other procedures known to one skilled in the art.

Pharmaceutical Compositions

The invention relates to a pharmaceutical composition comprising an isolated IL-34 polypeptide or a polynucleotide encoding thereof and an isolated M-CSF polypeptide or a polynucleotide encoding thereof.

The invention relates to a pharmaceutical composition comprising an isolated IL-34 polypeptide or a polynucleotide encoding thereof and an immunosuppressive drug.

The invention relates to a pharmaceutical composition comprising an isolated M-CSF polypeptide or a polynucleotide encoding thereof and an immunosuppressive drug.

The invention also relates to a pharmaceutical composition comprising a polypeptide as defined herein (or a nucleic acid encoding therefor, an expression vector or a host cell as above defined) and an immunosuppressive drug for use in inducing and/or maintaining immune tolerance in a patient in need thereof.

The invention further relates to a pharmaceutical composition comprising a polypeptide as defined herein (or a nucleic acid encoding therefor, an expression vector or a host cell as above defined) and an immunosuppressive drug for use in preventing or reducing transplant rejection in a patient in need thereof.

The invention relates to a pharmaceutical composition comprising a polypeptide as defined herein (or a nucleic acid encoding therefor, an expression vector or a host cell as above defined) and an immunosuppressive drug for use in a patient in need thereof.

Pharmaceutical compositions comprising a polypeptide of the invention include all compositions wherein the polypeptide is contained in an amount effective to achieve the intended purpose. In addition, the pharmaceutical compositions may contain suitable physiologically acceptable carriers comprising excipients and auxiliaries which facilitate processing of the active compounds into preparations which can be used pharmaceutically.

The term "physiologically acceptable carrier" is meant to encompass any carrier, which does not interfere with the effectiveness of the biological activity of the active ingredient and that is not toxic to the host to which is administered. Suitable physiologically acceptable carriers are well known in the art and are described for example in Remington's Pharmaceutical Sciences (Mack Publishing Company, Easton, USA, 1985), which is a standard reference text in this field. For example, for parenteral administration, the above active ingredients may be formulated in unit dosage form for injection in vehicles such as saline, dextrose solution, serum albumin and Ringer's solution.

Besides the physiologically acceptable carrier, the pharmaceutical compositions of the invention can also comprise minor amounts of additives, such as stabilizers, excipients, buffers and preservatives. The pharmaceutical composition of the invention may further comprise an immunosuppressive drug.

In one embodiment, the immunosuppressive drug is selected from the group consisting of cytostatics such as mammalian target of rapamycin (mTOR) inhibitors and rapamycin (sirolimus); alkylating agents (cyclophosphamide) and antimetabolites (azathioprine, mercaptopurine and methotrexate); therapeutic antibodies (such as anti-CD4OL monoclonal antibodies, anti-IL-2R monoclonal antibodies, anti-CD3 monoclonal antibodies, anti-lymphocyte globulin (ALG) and anti-thymocyte globulin (ATG)); calcineurin inhibitors (cyclosporine); glucocorticoids and mycophenolate mofetil.

In one embodiment, the immunosuppressive drug is rapamycin (sirolimus).

The polypeptides of the invention may be administered by any means that achieve the intended purpose. For example, administration may be achieved by a number of different routes including, but not limited to subcutaneous, intravenous, intradermal, intramuscular, intraperitoneal, intracerebral, intrathecal, intranasal, oral, rectal, transdermal, buccal, topical, local, inhalant or subcutaneous use. Parenteral and topical routes are particularly preferred.

Dosages to be administered depend on individual needs, on the desired effect and the chosen route of administration. It is understood that the dosage administered will be dependent upon the age, sex, health, and weight of the recipient, concurrent treatment, if any, frequency of treatment, and the nature of the effect desired. The total dose required for each treatment may be administered by multiple doses or in a single dose.

The doses used for the administration can be adapted as a function of various parameters, and in particular as a function of the mode of administration used, of the relevant pathology, or alternatively of the desired duration of treatment. For example, it is well within the skill of the art to start doses of the compounds at levels lower than those required to achieve the desired therapeutic effect and to gradually increase the dosage until the desired effect is achieved. However, the daily dosage of the polypeptides may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 10 mg/kg of body weight per day.

In one embodiment, the immunosuppressive drug is administered to the patient in need thereof at a decreased dose (comparatively to the dose usually administered)

In one embodiment, the immunosuppressive drug is administered to the patient in need thereof at a suboptimal dose.

In a particular embodiment, rapamycin (sirolimus) is administered to the patient in need thereof at a suboptimal dose.

In one aspect, the invention relates to a method for inducing and/or maintaining immune tolerance in a patient in need thereof, comprising a step of administering to said patient a therapeutically effective amount of an IL-34 polypeptide or a polynucleotide encoding therefor.

In another aspect, the invention relates to a method for inducing and/or maintaining immune tolerance in a patient in need thereof, comprising a step of administering to said patient a therapeutically effective amount of a M-CSF polypeptide or a polynucleotide encoding therefor.

In another aspect, the invention relates to a method for inducing and/or maintaining immune tolerance in a patient in need thereof, comprising a step of administering to said patient a therapeutically effective amount of a M-CSF polypeptide or a polynucleotide encoding therefor and a therapeutically effective amount of a IL-34 polypeptide or a polynucleotide encoding therefor.

In one embodiment, the method for inducing and/or maintaining immune tolerance in a patient in need thereof, comprising a step of administering to said patient a therapeutically effective amount of an IL-34 polypeptide or a polynucleotide encoding thereof and of a therapeutically effective amount an immunosuppressive agent.

In one embodiment, the method for inducing and/or maintaining immune tolerance in a patient in need thereof, comprising a step of administering to said patient a therapeutically effective amount of a M-CSF polypeptide or a polynucleotide encoding thereof and of a therapeutically effective amount an immunosuppressive agent.

In one embodiment, the method for inducing and/or maintaining immune tolerance in a patient in need thereof, comprising a step of administering to said patient a therapeutically effective amount of a M-CSF polypeptide or a polynucleotide encoding thereof, a therapeutically effective amount of a M-CSF polypeptide or a polynucleotide encoding thereof and of a therapeutically effective amount an immunosuppressive agent.

In another aspect, the invention relates to a method for preventing or reducing transplant rejection in a patient in need thereof, comprising a step of administering to said patient a therapeutically effective amount of an IL-34 polypeptide or a polynucleotide encoding therefor simultaneously and/or subsequently to the transplantation.

In another aspect, the invention relates to a method for preventing or reducing transplant rejection in a patient in need thereof, comprising a step of administering to said patient a therapeutically effective amount of a M-CSF polypeptide or a polynucleotide encoding therefor simultaneously and/or subsequently to the transplantation.

In another aspect, the invention relates to a method for preventing or reducing transplant rejection in a patient in need thereof, comprising a step of administering to said patient a therapeutically effective amount of a M-CSF polypeptide or a polynucleotide encoding therefor, a therapeutically effective amount of a IL-34 polypeptide or a polynucleotide encoding therefor simultaneously and/or subsequently to the transplantation.

In one embodiment, the method for preventing or reducing transplant rejection in a patient in need thereof, comprising a step of administering to said patient a therapeutically effective amount of an IL-34 polypeptide or a polynucleotide encoding therefor and of a therapeutically effective amount an immunosuppressive agent simultaneously and/or subsequently to the transplantation.

In one embodiment, the method for preventing or reducing transplant rejection in a patient in need thereof, comprising a step of administering to said patient a therapeutically effective amount of an M-CSF polypeptide or a polynucleotide encoding therefor and of a therapeutically effective amount an immunosuppressive agent simultaneously and/or subsequently to the transplantation.

In one embodiment, the method for preventing or reducing transplant rejection in a patient in need thereof, comprising a step of administering to said patient a therapeutically effective amount of an M-CSF polypeptide or a polynucleotide encoding therefor, a therapeutically effective amount of a IL-34 polypeptide or a polynucleotide encoding therefor and a therapeutically effective amount an immunosuppressive agent simultaneously and/or subsequently to the transplantation.

As used herein, the term "simultaneously" means that the polypeptide of interest is administered to the recipient patient the same day that the transplantation.

As used herein, the term "subsequently" means that the polypeptide of interest is administered to the recipient patient after the transplantation, for instance 2, 3, 4, 5, 6 or 7 days following the transplantation.

In a further aspect, the invention relates to a method for improving survival of a transplant, said method comprising a step of (pre-)culturing the transplant with a culture medium comprising an effective amount of an IL-34 polypeptide or a polynucleotide encoding therefor and/or a M-CSF polypeptide or a polynucleotide encoding therefor.

As used herein, the term "culture medium" refers to a liquid medium suitable for the ex vivo culture of mammalian cells, tissues or organs.

The culture medium used by the invention may be a water-based medium that includes a combination of substances such as salts, nutrients, minerals, vitamins, amino acids, nucleic acids, proteins such as cytokines, growth factors and hormones, all of which are needed for cell, tissue or organ survival.

For example, a culture medium according to the invention may be a synthetic tissue culture medium such as the RPMI (Roswell Park Memorial Institute medium) or the CMRL-1066 (Connaught Medical Research Laboratory) for human use, supplemented with the necessary additives.

In a preferred embodiment, the culture medium of the invention is free of animal-derived substances. In a preferred embodiment, the culture medium of the invention consists essentially of synthetic compounds, compounds of human origin and water. Advantageously, said culture medium can be used for culturing cells according to good manufacturing practices (under "GMP" conditions).

In a further aspect, the invention relates to a method for improving survival of the transplant in a transplanted patient (recipient), said method comprising a step of administering a therapeutically effective amount of an IL-34 polypeptide or a polynucleotide encoding therefor to said patient and/or a M-CSF polypeptide or a polynucleotide encoding therefor.

In one embodiment, the IL-34 polypeptide or a polynucleotide encoding therefor and/or the M-CSF polypeptide or a polynucleotide encoding therefor is administrated to the patient in the very first phase of transplantation.

In still another aspect, the invention relates to a method for preventing or treating autoimmune diseases, unwanted or anti-therapeutic proteins immune responses and allergies in a patient in need thereof, comprising a step of administering to said patient a therapeutically effective amount of an IL-34 polypeptide or a polynucleotide encoding therefor and/or a M-CSF polypeptide or a polynucleotide encoding therefor.

In one embodiment, the method for preventing or treating autoimmune diseases, alloimmune responses and allergies in a patient in need thereof, comprising a step of administering to said patient a therapeutically effective amount of an IL-34 polypeptide or a polynucleotide encoding thereof and/or a M-CSF polypeptide or a polynucleotide encoding therefor and of a therapeutically effective amount an immunosuppressive agent.

By "therapeutically effective amount" is meant an amount sufficient to achieve a concentration of polypeptide which is capable of preventing, treating or slowing down the disease to be treated. Such concentrations can be routinely determined by those of skilled in the art. The amount of the polypeptide actually administered will typically be determined by a physician or a veterinarian, in the light of the relevant circumstances, including the condition to be treated, the chosen route of administration, the actual compound administered, the age, weight, and response of the patient, the severity of the subject's symptoms, and the like. It will also be appreciated by those of skilled in the art that the dosage may be dependent on the stability of the administered polypeptide.

In one embodiment, the treatment with an IL-34 polypeptide and/or a M-CSF polypeptide is administered in more than one cycle, i.e. the administration of an IL-34 polypeptide and/or a M-CSF polypeptide is repeated at least once.

For example, 2 to 10 cycles or even more, depending on the specific patient status and response, may be administered. The intervals, i.e. the time between the start of two subsequent cycles, are typically several days.

Kit-of-Part Compositions

The IL-34 polypeptide and the M-CSF polypeptide may be combined within one formulation and administered simultaneously. The invention thus relates to a kit-of-part composition comprising an isolated IL-34 polypeptide or a polynucleotide encoding therefor and a M-CSF polypeptide or a polynucleotide encoding therefor.

The IL-34 polypeptide and/or the M-CSF polypeptide and the immunusuppressive drug may be combined within one formulation and administered simultaneously. However, they may also be administered separately, using separate compositions. It is further noted that they may be administered at different times.

The invention thus relates to a kit-of-part composition comprising an isolated IL-34 polypeptide or a polynucleotide encoding therefor and/or a M-CSF polypeptide or a polynucleotide encoding therefor and an immunosuppressive drug.

The invention also relates to a kit-of-part composition comprising an isolated IL-34 polypeptide or a polynucleotide encoding therefor and/or a M-CSF polypeptide or a polynucleotide encoding therefor and an immunosuppressive drug for use in inducing and/or maintaining immune tolerance in a patient in need thereof.

The invention also relates to a kit-of-part composition comprising an isolated IL-34 polypeptide or a polynucleotide encoding therefor and/or a M-CSF polypeptide or a polynucleotide encoding therefor and an immunosuppressive drug for use in preventing or reducing transplant rejection in a patient in need thereof.

The invention further relates to a kit-of-part composition comprising an isolated IL-34 polypeptide or a polynucleotide encoding therefor and/or a M-CSF polypeptide or a polynucleotide encoding therefor and an immunosuppressive drug for use in preventing or treating autoimmune diseases, alloimmune responses and allergies in a patient in need thereof.

The terms "kit", "product" or "combined preparation", as used herein, define especially a "kit-of-parts" in the sense that the combination partners as defined above can be dosed independently or by use of different fixed combinations with distinguished amounts of the combination partners, i.e. simultaneously or at different time points. The parts of the kit of parts can then, e.g., be administered simultaneously or chronologically staggered, that is at different time points and with equal or different time intervals for any part of the kit of parts. The ratio of the total amounts of the combination partners to be administered in the combined preparation can be varied. The combination partners can be administered by the same route or by different routes. When the administration is sequential, the first partner may be for instance administered 1, 2, 3, 4, 5, 6, 7, days before the second partner.

Prognostic Methods of the Invention

In a further aspect, the invention relates to an in vitro method for determining whether a patient is at risk of transplant rejection autoimmune diseases, unwanted immune response against therapeutic proteins or allergies, comprising a step of determining the expression level of IL-34 in a biological sample obtained from said patient, wherein the presence of IL-34 is indicative of a reduced risk of transplant rejection autoimmune diseases, unwanted immune response against therapeutic proteins or allergies.

In a further aspect, the invention relates to an in vitro method for determining whether a patient is at risk of transplant rejection autoimmune diseases, unwanted immune response against therapeutic proteins or allergies, comprising a step of determining the expression level of M-CSF in a biological sample obtained from said patient, wherein the presence of M-CSF is indicative of a reduced risk of transplant rejection autoimmune diseases, unwanted immune response against therapeutic proteins or allergies.

As used herein, the term "risk" refers to the probability that an event will occur over a specific time period, such as the onset of transplant rejection, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a patient compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion.

"Risk determination" in the context of the invention encompasses making a prediction of the probability, odds, or likelihood that an event may occur. Risk determination can also comprise prediction of future clinical parameters, traditional laboratory risk factor values, such age, sex mismatch, HLA-testing, etc. . . . ; either in absolute or relative terms in reference to a previously measured population. The methods of the invention may be used to make categorical measurements of the risk of transplant rejection, thus defining the risk spectrum of a category of transplanted patient defined as being at risk of transplant rejection.

In a still further aspect, the invention relates to an in vitro method for determining whether a transplanted patient (recipient) is tolerant, comprising a step of determining the expression level of IL-34 in a biological sample obtained from said transplanted patient, wherein the presence of IL-34 is indicative of tolerance.

In a still further aspect, the invention relates to an in vitro method for determining whether a transplanted patient (recipient) is tolerant, comprising a step of determining the expression level of M-CSF in a biological sample obtained from said transplanted patient, wherein the presence of M-CSF is indicative of tolerance.

As used herein, the term "determining" includes qualitative and/or quantitative detection (i.e. detecting and/or measuring the expression level) with or without reference to a control or a predetermined value. As used herein, "detecting" means determining if IL-34 or M-CSF is present or not in a biological sample and "measuring" means determining the amount of IL-34 or M-CSF in a biological sample. Typically the expression level may be determined for example by immunoassays such as an ELISA performed on a biological sample.

As used herein, the term "biological sample" has its general meaning in the art and refers to any sample which may be obtained from a patient for the purpose of in vitro evaluation. A preferred biological sample is a blood sample (e.g. whole blood sample, serum sample, or plasma sample).

Methods for Determining the Expression Level of the Biomarker of the Invention

Determination of the expression level of IL-34 or M-CSF may be performed by a variety of techniques. Generally, the expression level as determined is a relative expression level.

For example, the determination of the expression level of IL-34 or M-CSF may comprise a step of contacting the biological sample with selective reagents such as antibodies, and thereby detecting the presence, or measuring the amount, of polypeptide of interest originally in said biological sample. Contacting may be performed in any suitable device, such as a plate, microtiter dish, test tube, well, glass, column, and so forth.

In one embodiment, the contacting is performed on a substrate coated with the reagent. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as an antibody-antigen complex, to be formed between the reagent and the polypeptides of the biological sample.

The presence of the IL-34 polypeptide or M-CSF polypeptide may be detected using standard electrophoretic and immunodiagnostic techniques, including immunoassays such as competition, direct reaction, or sandwich type assays. Such assays include, but are not limited to, Western blots; agglutination tests; enzyme-labelled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith. Labels are known in the art that generally provide (either directly or indirectly) a signal.

As used herein, the term "labelled" with regard to the antibody or aptamer, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or indocyanine (Cy5), to the antibody or aptamer, as well as indirect labelling of the probe or antibody (e.g., horseradish peroxidise, HRP) by reactivity with a detectable substance. An antibody or aptamer may be also labelled with a radioactive molecule by any method known in the art. For example, radioactive molecules include but are not limited radioactive atom for scintigraphic studies such as 1123, 1124, In111, Re186 and Re188. The aforementioned assays generally involve separation of unbound protein in a liquid phase from a solid phase support to which antigen-antibody complexes are bound. Solid supports which may be used in the practice of the invention include substrates such as nitrocellulose (e.g., in membrane or microtiter well form);

polyvinylchloride (e.g., sheets or microtiter wells); polystyrene latex (e.g., beads or microtiter plates); polyvinylidine fluoride; diazotized paper; nylon membranes; activated beads, magnetically responsive beads, etc.

More particularly, an ELISA method may be used, wherein the wells of a microtiter plate are coated with an antibody against the protein to be tested. A biological sample containing or suspected of containing the biomarker is then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art.

The selective reagent is generally an antibody that may be polyclonal or monoclonal, preferably monoclonal. Polyclonal antibodies directed against IL-34 are well known from the skilled man in the art such as the antibodies commercialized by Abnova PAB16574.

Monoclonal antibodies directed against IL-34 are also well known such as the monoclonal antibody commercialized by Abnova MAB10698.

Additionally, IL-34 ELISA Kits are also well known such as those commercialized by Abnova KA2217 Kit or by R&D Systems (Human IL-34 Quantikine ELISA).

The selective reagent is generally an antibody that may be polyclonal or monoclonal, preferably monoclonal. Polyclonal antibodies directed against M-CSF are well known from the skilled man in the art such as the antibodies commercialized by Abcam (ab9693).

Monoclonal antibodies directed against M-CSF are also well known such as the monoclonal antibody commercialized by MyBioSource (MBS690427).

Additionally, M-CSF ELISA Kits are also well known such as those commercialized by R&D Systems (Human M-CSF Quantikine ELISA).

In a particular embodiment, the expression level of IL-34 or M-CSF is determined by measuring the concentration of IL-34 or M-CSF in said biological sample.

Accordingly, the methods according to the invention comprise a step of contacting the blood sample with a binding partner capable of selectively interacting with IL-34 polypeptide or M-CSF polypeptide in said blood sample.

The binding partner may be generally an antibody that may be polyclonal or monoclonal, preferably monoclonal. Polyclonal antibodies directed against IL-34 or M-CSF can be raised according to known methods by administering the appropriate antigen or epitope to a host animal selected, e.g., from pigs, cows, horses, rabbits, goats, sheep, and mice, among others. Various adjuvants known in the art can be used to enhance antibody production.

Monoclonal antibodies of the invention can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al., 1985). Alternatively, techniques described for the production of single chain antibodies (see e.g. U.S. Pat. No. 4,946,778) can be adapted to produce single chain antibodies. Antibodies useful in practicing the present invention also include fragments including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed to allow rapid identification of fragments having the desired specificity. For example, phage display of antibodies may be used. In such a method, single-chain Fv (scFv) or Fab fragments are expressed on the surface of a suitable bacteriophage, e. g., M13. Briefly, spleen cells of a suitable host, e. g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e. g., bacteria, the phage displays the antibody fragment. Phage display of antibodies may also be provided by combinatorial methods known to those skilled in the art. Antibody fragments displayed by a phage may then be used as part of an immunoassay.

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of conformationally constrained antibody variable regions displayed by a platform protein, such as E. coli Thioredoxin A, that are selected from combinatorial libraries by two hybrid methods (Colas et al., 1996).

In other embodiments, measuring the concentration of IL-34 or M-CSF may also include separation of the proteins: centrifugation based on the protein's molecular weight; electrophoresis based on mass and charge; HPLC based on hydrophobicity; size exclusion chromatography based on size; and solid-phase affinity based on the protein's affinity for the particular solid-phase that is use. Once separated, IL-34 or M-CSF may be identified based on the known "separation profile" e. g., retention time, for that protein and measured using standard techniques. Alternatively, the separated proteins may be detected and measured by, for example, a mass spectrometer.

Methods for Adjusting an Immunosuppressive Treatment

The invention further provides methods for developing personalized treatment plans. Information gained by way of the methods described above can be used to develop a personalized treatment plan for a transplant recipient.

Accordingly, in a further aspect, the invention relates to a method for adjusting the immunosuppressive treatment administered to a patient in need thereof, comprising the following steps of (i) performing the method for determining the risk according to the invention, and (ii) adjusting the immunosuppressive treatment.

The methods can be carried out by, for example, using any of the methods for determining risk described above and, in consideration of the results obtained, designing a treatment plan for the transplant recipient. If IL-34 or M-CSF is not present in the biological sample obtained from a patient of interest, this indicates that said patient is at risk for an undesirable clinical outcome (e.g., transplant rejection). Therefore, said patient is a candidate for treatment with an effective amount of an immunosuppressive treatment (e.g. by an anti-rejection agent). On the contrary, the presence of IL-34 or M-CSF in the biological sample is indicative of a reduced risk of transplant rejection. Moreover, depending on the expression level IL-34 or M-CSF (i.e. low level or high level of IL-34 or M-CSF in the analyzed biological sample), the patient may require a treatment regime that is more or less aggressive than a standard regimen, or it may be determined that the patient is best suited for a standard regimen. For instance, a patient with a high level of IL-34 or M-CSF may avoid an immunosuppressive treatment (or require a less aggressive regimen) and their associated side effects.

The invention will be further illustrated by the following figures and examples. However, these examples and figures should not be interpreted in any way as limiting the scope of the present invention.

FIGURES

FIG. 1: Increased IL-34 expression in grafts and splenic CD8+ Tregs following treatment with CD40Ig. A. FACS Aria-sorted CD8+CD45RClow Tregs from spleen of naive or 120 days old AdCD40Ig-treated recipients (n=6) were analysed for IL-34 mRNA expression by quantitative RT-PCR. Cardiac grafts (B) and spleen (C) from AdCD40Ig-treated recipients at day 5 (n=3) and 120 (n=7) after transplantation was compared with grafts from non-treated-recipients at day 5 (n=8), day 7 (n=8) and day 120 (n=6) and native hearts from naive animals (n=7) for IL-34 mRNA expression. (D) CD8+CD45RC$^{low}$ Tregs were sorted from the spleen of CD40Ig-treated rats and analyzed for their expression of IL-34 (black) after 7 hours stimulation with PMA ionomycin (24 µg/mL). Grey-filled histogram represents the isotype control staining. Mann Whitney, *p<0.05, ** p<0.01.

Figure 2:
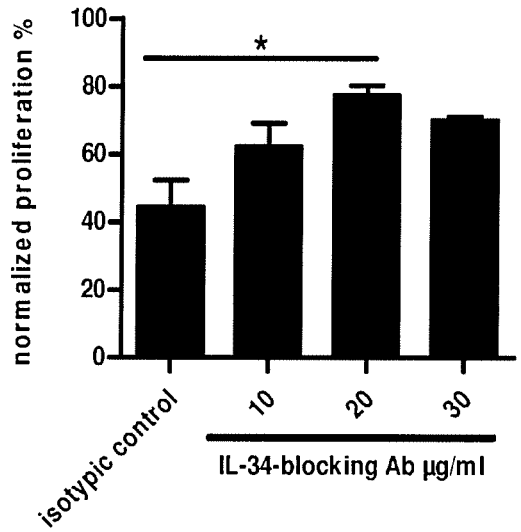
Figure 2:
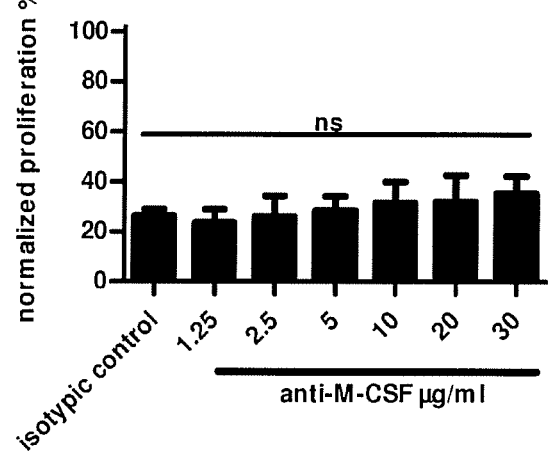
Figure 2:
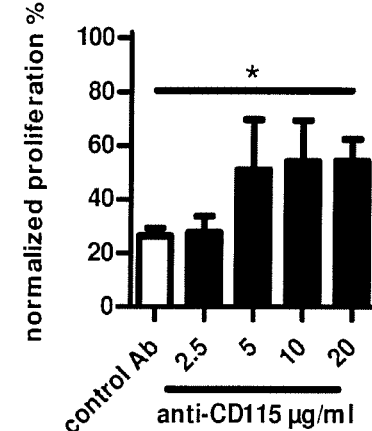

FIG. 2: IL-34 and CD115, but not M-CSF, were involved in CD8+CD45RClow Treg-mediated suppression. The relative proportion of CFSE-labeled LEW.1A dividing CD4+CD25− T cells stimulated with donor LEW.1W pDCs was analyzed after 6 days of culture, in the presence of LEW.1A CD8+CD45RClow Tregs at a 1:1 effector: suppressor ratio. The proliferation after addition of an anti-IL-34-blocking Ab (A), an anti-M-CSF blocking Ab (B) or an anti-CD115 blocking Ab (C) was evaluated compared to isotypic control (n=4 in triplicates). Results are expressed as mean±SEM of normalized percentage of proliferation vs. proliferation in the absence of CD8+ Tregs (100%).*, p<0.01.

Figure 3:
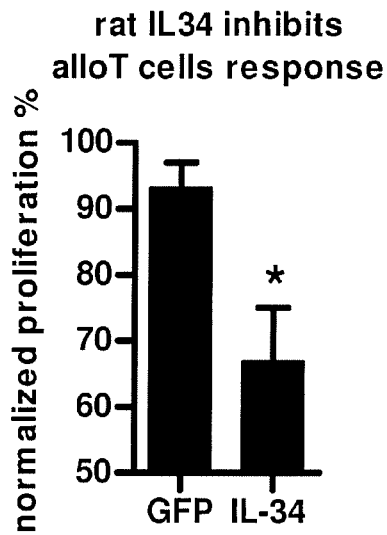
Figure 3:
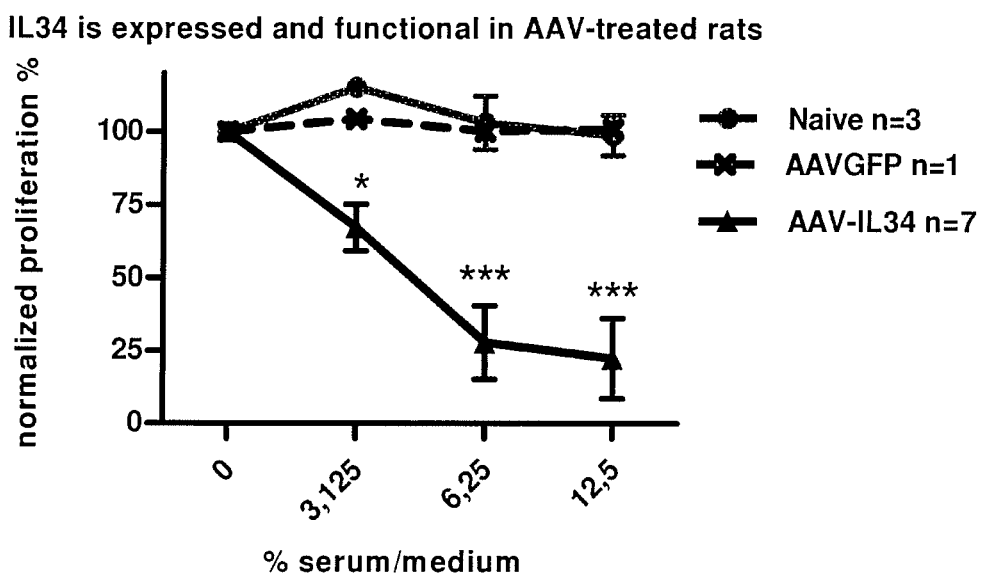

FIG. 3: Detection of IL-34 using an AAV-IL-34 and inhibition of allo-T cell responses. A. Supernatants of AAV- IL-34 or AAV-GFP-transduced cells were tested for suppression of CD4+CD25− T cell proliferation in response to allogeneic pDCs and analysed by flow cytometry for CFSE dilution after 5 days of culture. CD8+ Tregs were used as positive control of suppression. n=3 in duplicates; Results are expressed as mean±SEM of normalized percentage of proliferation vs. proliferation in the absence of CD8+ Tregs (100%). Representative histogram of 1 experiment; filled grey: proliferation of CD4+ T cells cocultured with pDC with 20% AAVGFP-transduced cell supernatent; black line: with 20% AAV-IL-34-transduced cells supernatant. B. Serial dilution of sera from AAV-IL-34 or AAV-GFP-treated rats or naive animals were tested for suppression of CD4+CD25− T cell proliferation in response to allogeneic pDCs and analysed by flow cytometry for CFSE dilution after 5 days of culture. CD8+ Tregs were used as positive control of suppression. n=3 in duplicates; Results are expressed as mean±SEM of normalized percentage of proliferation vs. proliferation in the absence of CD8+ Tregs (100%). *, $p<0.01$; , $p<0.001$; *, $p<0.0001$ vs. sera from naïve animals.

Figure 4:
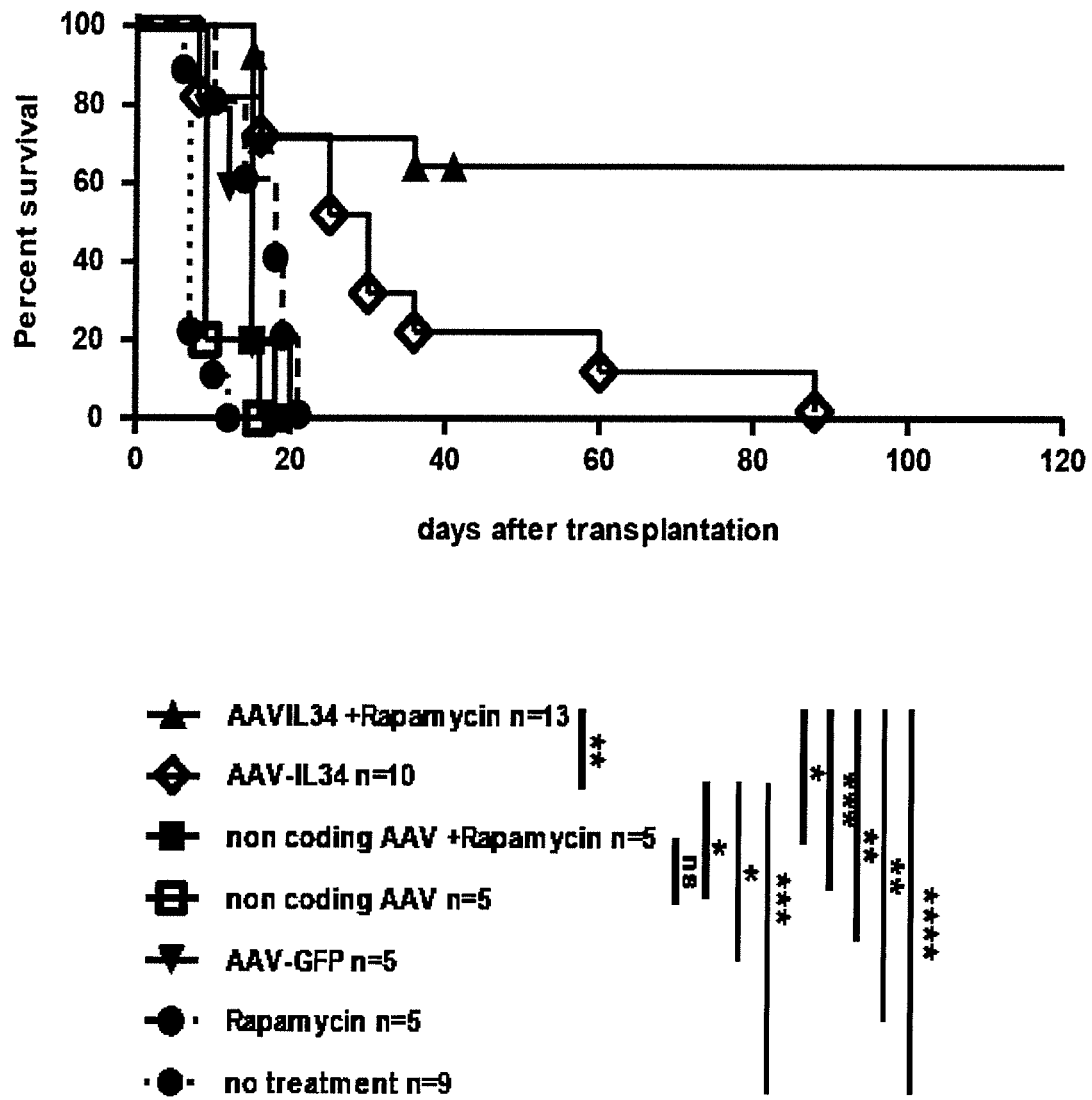

FIG. 4: IL-34 gene transfer prolongs allograft survival in a dominant manner. Recipients received intravenously $10^{12}$ vg/rat of AAV-IL-34 or non-coding AAV or untreated, were grafted 30 days later with no additional treatment or in combination with suboptimal dose of rapamycin (14 days, starting day 0). Graft survival was evaluated by palpation through the abdominal wall. ***$p<0.0001$.

Figure 5:
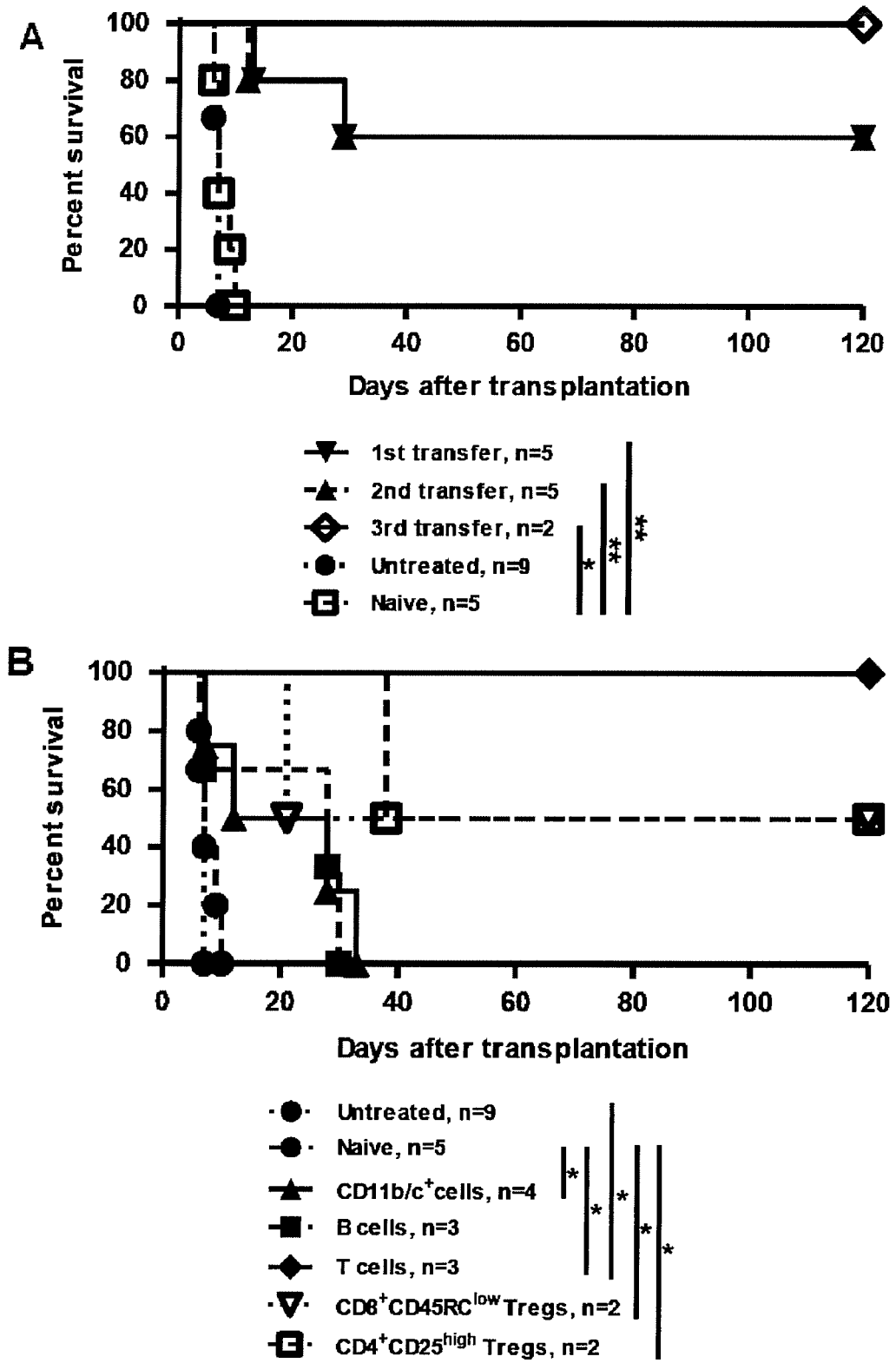

FIG. 5: Serial tolerance mediated by Tregs after IL-34 induction. A. LEW.1A recipients were sublethally irradiated (4.5 Gy) at day −1 and received heart allografts and i.v. injections of $1,5.10^8$ splenocytes from long surviving recipient or naive animals at day 0. Graft survival was monitored by abdominal palpation. B. LEW.1A recipients were sublethally irradiated (4.5 Gy) at day −1 and received heart allografts and i.v. injections of total splenocytes or purified sub-populations (T cells:$4.10^7$; B cells:$6.10^7$, CD11b/c+ cells:$1,5.10^7$; CD8+CD45RC$^{low}$ Tregs:$4\times10^6$; CD4+CD25$^{high}$ Tregs: $4\times10^6$) from long surviving recipient at day 0. Graft survival was monitored by abdominal palpation. Log Rank test, ** $p<0.01$, *$p<0.05$.

Figure 6:
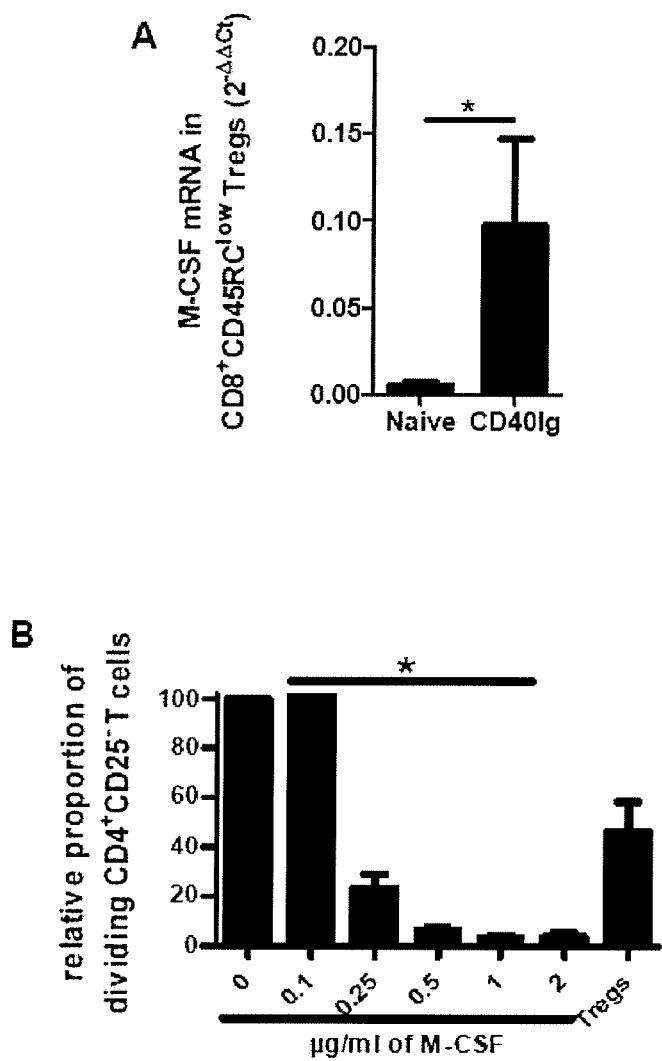

FIG. 6: M-CSF mediated dose dependent suppression of anti-donor effector CD4+CD25− T cells responses. (A) FACS Aria-sorted CD8+CD45RC$^{low}$ Tregs from spleen of naive or 120 days old AdCD40Ig-treated recipients (n=6) were analysed for M-CSF mRNA expression by quantitative RT-PCR. *$p<0.05$. (B) Rat M-CSF (0.1 to 2 µg/ml final concentration) was tested for suppressive activity on CFSE-labelled CD4+CD25− T-cell proliferation after 6 days of culture. CD8+ Tregs were used as positive control of suppression. n=3 in triplicates. Results are expressed as mean±SEM of normalized percentage of proliferation vs. proliferation in the absence of CD8+ Tregs (100%). *, $p<0.01$.

Figure 7A:
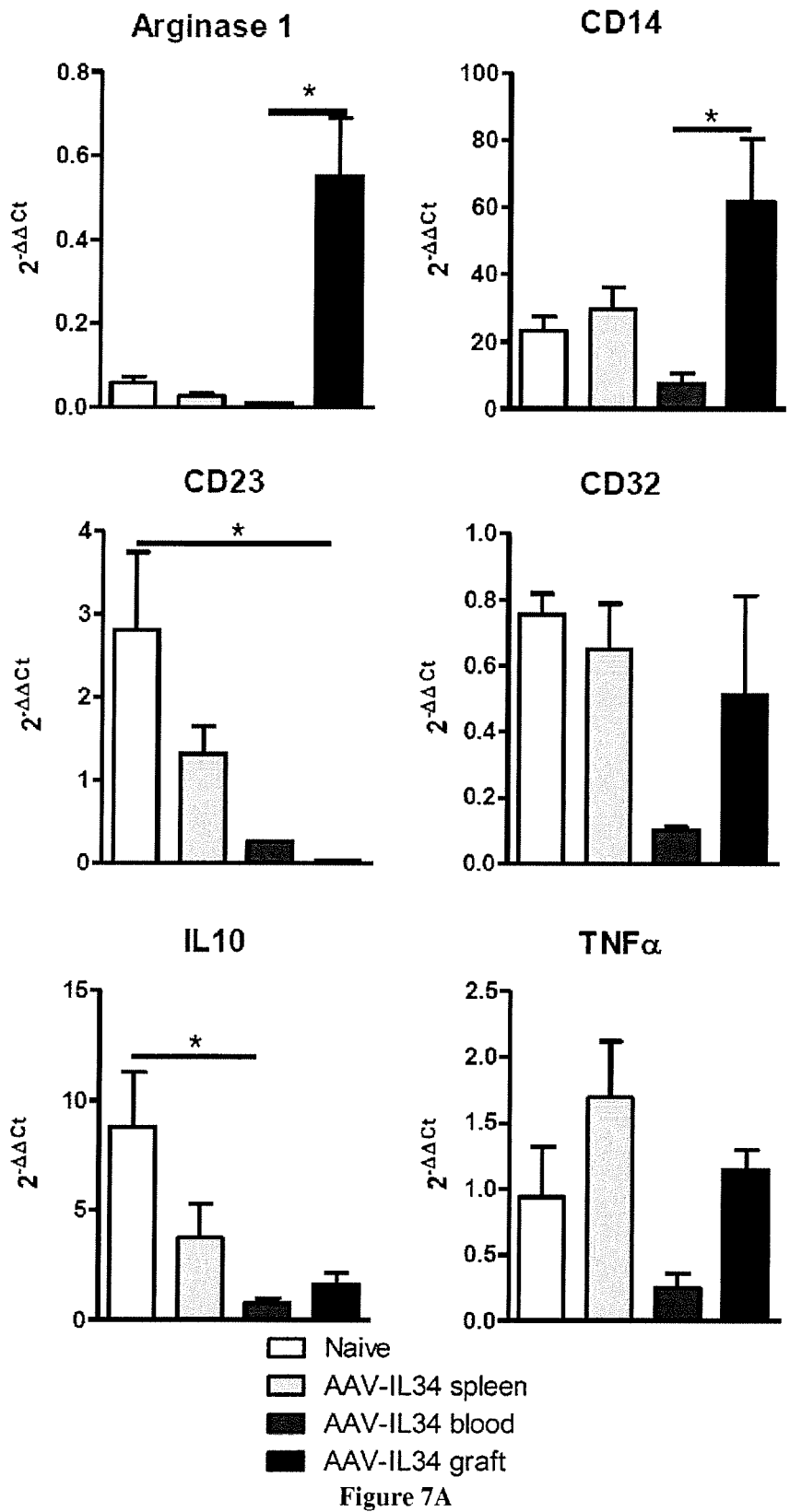
Figure 7B:
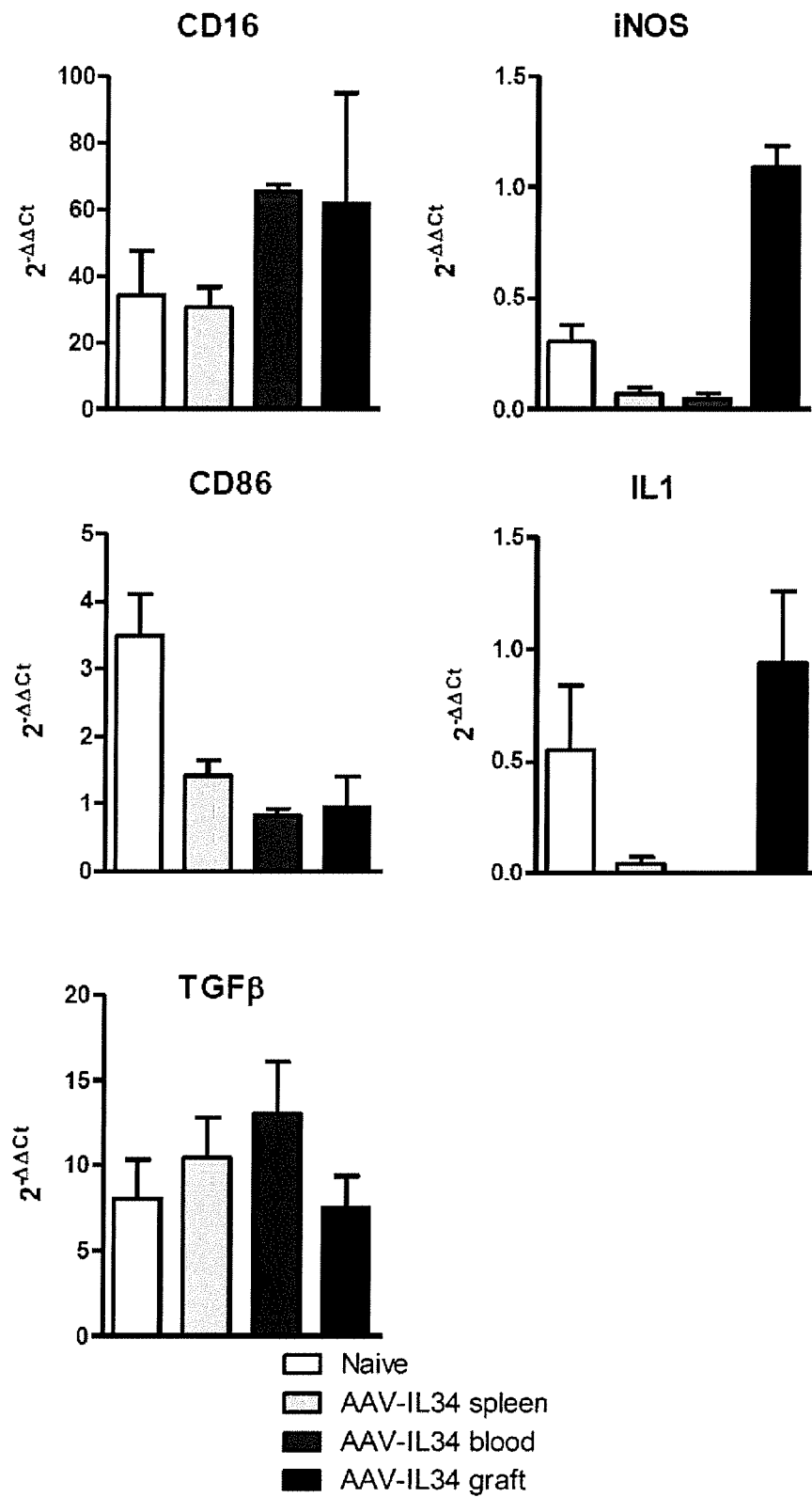

FIGS. 7A-B: Transcript accumulation in macrophages following IL34 treatment. mRNA expression was assessed by real-time quantitative PCR on sorted macrophages from untreated spleen or AAV-IL34-treated spleen, blood and graft of recipients at day 15 post-transplantation. Results are normalized to HPRT and expressed as $2^{-ddCT}$+/−SEM. Kruskal Wallis and Dunn's post test, *, $p<0.01$.

Figure 8:
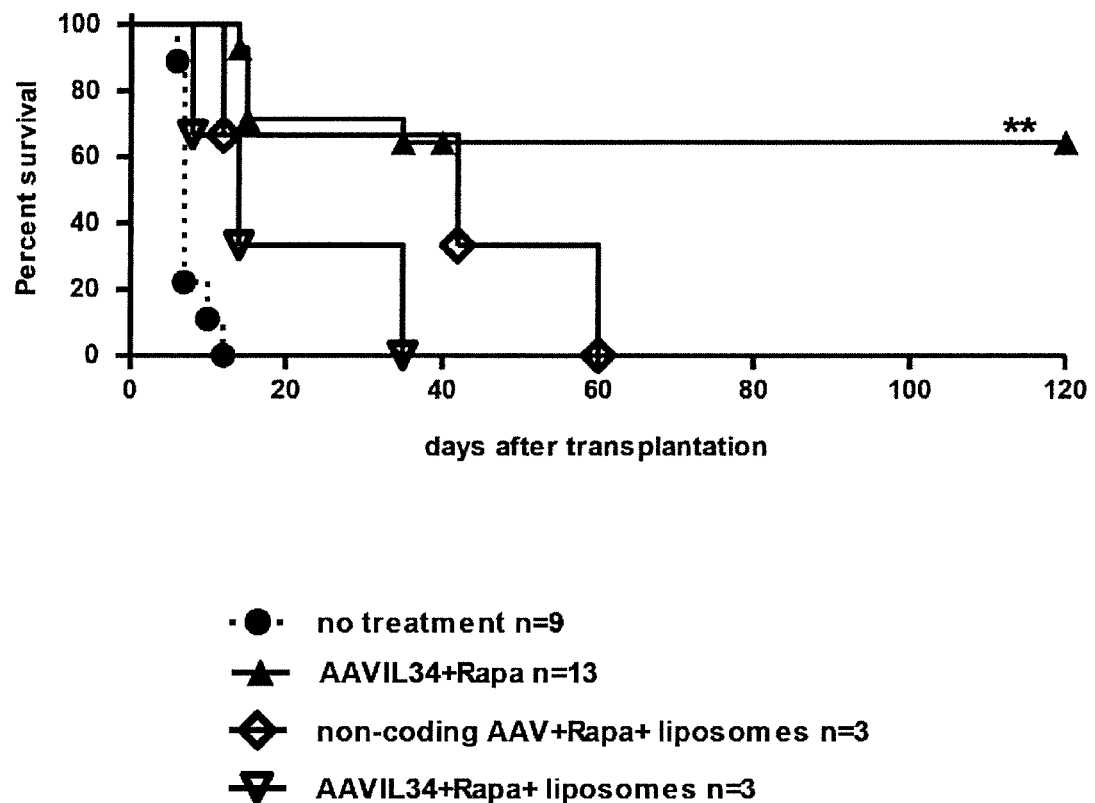

FIG. 8: Macrophages depletion resulted in allograft rejection following IL34 treatment. Recipients receiving at day −30 intravenously $10^{12}$ vg/rat of AAV-IL34 or non-coding AAV or were untreated with or without weekly intraperitoneal administration of clodronate liposomes from day −25 to day 3, and were grafted at day 0 in combination with suboptimal dose of rapamycin (10 days, starting day 0). Graft survival was evaluated by palpation through the abdominal wall. Log Rank test, **$p<0.01$.

Figure 9:
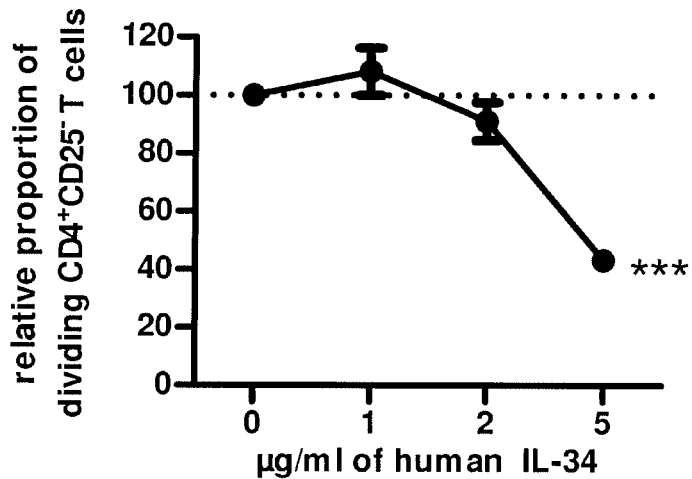
Figure 9:
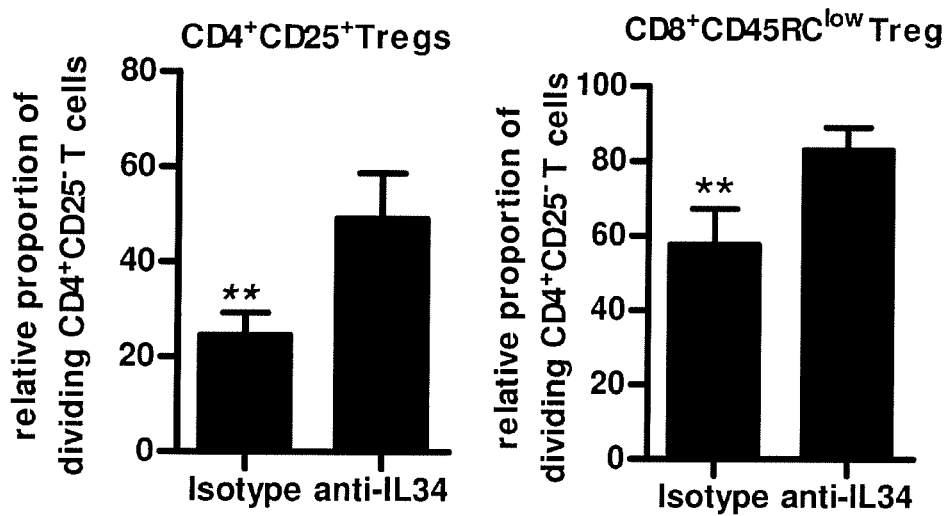

FIG. 9: IL34 is involved in human CD4+ and CD8+ Treg's suppressive activity, that can inhibit anti-donor immune responses. (A) Soluble IL34 was tested for suppression of CD4+CD25− T cell proliferation in response to allogeneic T-depleted PBMCs and analyzed by flow cytometry for CFSE dilution after 5 days of culture. n=2 to 5 in duplicates; Results are expressed as mean±SEM of relative proportion of dividing CD4+CD25− T cells. (B) The relative proportion of CFSE-labeled dividing CD4+CD25− T cells stimulated with allogeneic T-depleted PBMCs was analyzed after 5 days of culture, in the presence of CD8+CD45RC$^{low}$ or CD4+CD25$^{high}$ Tregs at 1:1 effector:suppressor ratios. The proliferation after addition of anti-IL34-blocking Ab was evaluated and compared to isotypic control (n=5-6 in triplicates). The proportion of dividing CD4+CD25− T cells in the control proliferation condition with allogeneic T-depleted PBMCs only represented approximately 60% of the cells on day 5 and was given a value of 100 in each experiment. Results are expressed as mean±SEM of the relative proportion of dividing CD4+CD25− T cells.

Example 1: Interleukin-34, a New Treg-Specific Cytokine Mediator of Transplant Tolerance Material & Methods Healthy volunteer blood collection and PBMC separation: Blood was collected from healthy donors, after informed consent was given, at the Etablissement Francais du Sang (Nantes, France). Blood was diluted 2-fold with PBS before PBMCs were isolated by Ficoll-Paque density-gradient centrifugation (Eurobio) at 2000 rpm for 30 min at room temperature without braking. Collected PBMCs were washed in 50 mL PBS at 1800 rpm for 10 min.

Animals and cardiac transplantation models: Heart allotransplantation was performed between whole MHC incompatible male LEW-1W (donors) and LEW-1A (recipients) rats as previously described (15). Heart survival was evaluated by palpation through the abdominal wall and heart beating was graded from +++ to −. The experiments were approved by the regional ethical committee for animal experimentation.

IL-34 quantitative RT-PCR: The isolation and retrotranscription of mRNA as well as the quantification of specific mRNA levels using Taqman technology after normalization to HPRT values have been described (15). The probes sequences were for forward primer 5' CTGGCTGTCCTC-TACCCTGA 3' (SEQ ID NO: 2) and for reverse primer 5' TGTCGTGGCAAGATATGGCAA 3' (SEQ ID NO: 3).

Cell sorting, monoclonal antibodies and flow cytometry: Macrophages were sorted on TCRαβ (R7/3) and TCRγδ (V65) negative cells, CD45RA-FITC (OX33), and CD11b/c-APC (OX42) positive cells. Naive LEW.1A CD4+CD25− T cells, LEW.1W pDC and LEW.1A CD8+CD45RC$^{low}$ Tregs subsets were sorted as previously described (16). The antibodies used for T cells (TCRαβ, clone R7/3), CD4+CD25− T cells (clones OX35 and OX39), CD8+ T cells (clone OX8), CD8+CD45RC$^{low}$ T cells (clones OX8 and OX22), and CD4+CD45R+85C7+ pDCs (clones His24, OX35 and 85C7) sorting were obtained from the European Collection of Cell Culture (Salisbury, UK). All biotin-labelled mAbs were visualized using Strepavidin-PE-Cy7 (BD Biosciences) or Streptavidin-Alexa405. Human CD4+CD25− T cells were sorted by gating on CD3+CD4+ CD25− cells (clones SKY7, L-200 and MA251), CD4+ Tregs by gating on CD25high and CD127low cells (clone HIL7-R M21), and CD8$^+$ Tregs by gating on CD3+CD4-CD45RClow cells (clone MT2). IL-34-Myc was detected using an anti-myc antibody (9E10, Sigma). IL-34, CD115, and MCSF were blocked with the anti-IL-34 (PAB16574, Abnova), anti-CD115 (MCA1898, Serotec) and anti-M-CSF (AB-416-NA, R and D system) antibodies. Antibodies against MHC-II (OX6), CD11b and CD45RA$^+$ B cells (OX33) were analysed to characterize cell's phenotype. Antibodies against CD3-PeCy7 (SKY7), CD4-PercPCy5.5 (L200), CD25-APCCy7 (M-A251), CD127-PE (HIL7-R M21, BD Bioscience), CD45RC-FITC (MT2, IQ Product), Foxp3-APC (236A/E7, ebiosciences) and IL34-PE (578416, R&D) were used to characterize human cell phenotypes. A FACS ARIA I (BD Biosciences, Mountain View, CA) was used to sort cells. A Canto II cytometer (BD Biosciences, Mountain View, CA) was used to measure fluorescence, and data were analyzed using the FLOWJO software (Tree Star, Inc. USA). Cells were first gated by their morphology excluding dead cells by selecting DAPI viable cells.

AAV generation and use in vitro and in vivo: Complete cDNA sequence of rat IL-34 containing Q81 (9), or GFP as control, were positionned downstream a RSV promotor. Plasmids were first tested in HEK293T cells transfected with lipofectamine reagent (Life Technologies, Carlsbad, Nouveau-Mexique). Cells were analysed for GFP and IL-34-myc expression 48 h later by FACS with anti-myc Ab. Then, plasmids were used to produce AAV vectors of serotype 8 (LTG platform, INSERM UMR 1089, Nantes). HEK293T cells were transduced with 10 000, 100 000 to 1 000 000 MOI vector genome copies/cell of AAV-IL-34 or AAV-GFP and 5 000 MOI AdLacZ. 24 h later, cells were harvested and analysed for IL-34-Myc expression by FACS, and supernatent was tested for suppression activity on CD4+ Tcells responding to allogeneic pDCs, at a 1/10 and 1/5 dilution. Recombinant AAV-IL-34 and AAV-GFP ($4.5.10^{10}$, $1.10^{12}$, and $2.10^{12}$ vector genomes/rat) vectors were injected i.v. in 4-weeks-old rats one month before transplantation to allow optimal expression from AAV vectors (23) Blood samples were taken for donor allospecific antibodies quantification.

Adoptive cell transfer: Rat cells were sorted as previously described (5, 8) by FACS Aria (BD Biosciences, Mountain View, CA) by gating on TCRαβ-APC (R7/3), CD45RA-FITC (OX33), and CD11b/c-biotin-Streptavidine PECy7 (OX42) positive cells. Recipients that received splenocytes from IL34-treated rats are defined as $1^{st}$ transferred and then iterative transfers were defined as $2^{nd}$-to $3^{rd}$ transferred. Total splenocytes ($1.5 \times 10^8$ cells) and FACS Aria-sorted CD45RA$^+$ B cells ($6 \times 10^7$), T cells ($4 \times 10^7$), CD11b/c$^+$ cells ($1.5 \times 10^7$), CD4$^+$CD25$^{high}$ Tregs ($4 \times 10^6$) or CD8$^+$ CD45RC$^{low}$ Tregs ($4 \times 10^6$) were adoptively transferred i. v. the day before heart transplantation into naive LEW-1A recipients that had received 4.5 Gy of whole-body irradiation the same day.

Mixed lymphocyte reaction: Naive Lewis 1A CD4$^+$ T cells, naïve Lewis 1W pDC, and AdCD40Ig-treated Lewis 1A CD8$^+$CD45RC$^{low}$ Tregs subsets were sorted as previously described (16). Serum from AAV-IL-34-treated, AdCD40Ig-treated recipients and naïve rats were added in coculture to reach 3.12%, 6.25%, and 12.5% final concentration. Supernatent of transduced cells was added to CD4$^+$ T cells and pDC from 10% to 20% final concentration for suppressive activity test. Rat IL-34, CD115 or M-CSF-blocking Ab or isotypic control were tested for blocking activity from 1.25 to 30 μg/ml in presence or not of CD8$^+$CD40Ig Tregs. M-CSF protein (ab56288, ABCAM) was tested from 0.1 to 2 μg/ml. Proliferation of CFSE-labelled CD4$^+$CD25$^-$ T cells was analyzed by flow cytometry 6 days later, by gating on TCR$^{+CD}$4$^+$ cells (R7/3-APC, Ox35-PECY7) among living cells (DAPI negative).

Sorted human CD4$^+$CD25$^-$ T cells were plated in triplicate with allogeneic human T-depleted PBMCs in 200 μl of complete RPMI-1640 medium in round or conic bottom 96-well plates, respectively, at 37° C. and 5% CO2. Human IL34 Ab was used at 50 μg/ml, and variable numbers of Tregs were added. Isotype control Ab were used at the highest concentration displayed in the respective graph. M-CSF protein (ab56288, ABCAM) was tested from 0.1 to 2 μg/ml. Soluble human IL34 (eBiosciences) was added at a concentration of 1, 2 or 5 μg/ml for the suppressive activity test.

Donor specific alloantibodies quantification: Donor spleens were digested by collagenase D, stopped with 400 μl EDTA 0.1 mM, and red cells were lysed. Serum of recipients were added to donor splenocytes at a dilution ⅛, and incubated with either anti-rat IgG-FITC (Jackson ImmunoResearch Labs INC, Baltimore, USA), anti-rat IgG1 (MCA 194, Serotec), anti-rat IgG2a (MCA 278, Serotec), or anti-rat IgG2b (STAR114F, Serotec) and anti-Ms Ig-FITC (115-095-164, Jackson ImmunoResearch). A FACS Canto (BD Biosciences, Mountain View, CA) was used to measure fluorescence, and data were analyzed using the FLOWJO software (Tree Star, Inc. USA). Geometric mean of fluorescence (MFI) of tested sera was divided by mean of 5 naive Lewis 1A sera MFI as control.

Statistical analysis: One Way ANOVA Kruskal Wallis test and Dunn's posttest was used for PCR and coculture experiments, Two-Way ANOVA test and Bonferroni posttests was applied for donor-directed antibodies, and splenocytes phenotype characterization, and Mantel Cox test was used to analyse survival curves.

Clodronate liposomes in vivo treatment: Clodronate liposomes for macrophage depletion were purchased from Vrije University, The Netherlands (www.clodronateliposomes.org) and prepared as recommended (5041). Briefly, 2.5 ml of suspended solution was administered weekly intra-peritonealy from day −25 to day 3.

Quantitative RT-PCR: Total RNA was isolated from cells using Trizol reagent (Invitrogen) or an RNeasy Mini Kit (Qiagen). RNA from macrophages was amplified with MessageAmpTMII aRNA Amplification Kit according to the manufacturer instructions (Life Technologies) and reverse transcripted with random primers and M-MLV reverse transcriptase (Life Technologies). Real-time PCR was done using the Fast SYBR Green technology in a 20 μL final reaction volume containing 10 μL of Master Mix 2X (Life Technologies), 0.6 μL of primers (10 μM), 1 μL of cDNA and 8.4 μL of water. The reaction was performed on the Applied Biosystems StepOne™ (Life Technologies). The thermal conditions were the following: 3 sec at 95° C., 30 sec at 60° C. and 15 sec at TM-5° C. with a final melting curve stage.

Results

IL-34 was expressed by splenic CD8$^+$CD45RC$^{low}$ Treg and the tolerant allograft: DNA microarray analysis of CD8$^+$CD40Ig Tregs vs. naive CD8$^+$CD45RC$^{low}$ Tregs from spleen, highlighted IL-34 upregulation (among the most upregulated genes) by CD8$^+$CD40Ig Tregs, with a fold change of 4.05. This upregulation was confirmed by qPCR with >11 fold increase of IL-34 mRNA expression in long-term splenic CD8$^+$CD40Ig Tregs compared with naive CD8$^+$CD45RC$^{low}$ Tregs ($p < 0.05$, FIG. 1A).

Looking at whole organs, IL-34 mRNA was expressed endogenously in spleen and heart of naive animals (as observed by Lin et al. (18)) (FIG. 1B), and slightly decreased during acute allograft rejection in both spleen and graft (NT, FIGS. 1B and 1C). In correlation with our previous observations that CD8+CD40Ig Tregs accumulated in the graft during the first week (16), IL-34 mRNA expression was significantly increased at day 5 in AdCD40Ig-treated graft and spleen (FIGS. 1B and 1C). This significant increase was still detectable in AdCD40Ig-treated graft 120 days after transplantation; however in the total spleen IL-34 mRNA level had return to normal.

To confirm the protein expression of IL-34, we labeled CD8+CD40Ig Tregs with a mouse anti-rat IL-34 antibody (Ab) that we generated. With this Ab, we confirmed the significant expression of IL-34 by CD8+CD40Ig Tregs compared to naive CD8+CD45RC$^{low}$ Tregs (FIG. 1D).

Altogether, these results demonstrated for the first time that IL-34 can be expressed by induced CD8+CD45RC$^{low}$ Tregs, as well as tolerated allograft. Moreover, the early expression of IL-34 in graft and spleen suggest its early involvement in the inhibition of acute graft rejection and thus the establishment of allograft tolerance.

IL-34 expressed by CD8+CD45RC$^{low}$ Treg, but not M-CSF, is involved in Treg-mediated suppression: We previously demonstrated that CD8+CD40Ig Tregs suppress anti-donor proliferation of CD4+ effector T cells in response to allogeneic pDCs ex vivo (16). In addition, we demonstrated the involvement of IFNγ and FGL2 in this process; however some suppression remained after blockade of IFNγ and FGL2 inhibitory effect (15, 16). To address whether IL-34 was involved in CD8+CD40Ig Treg suppression, we tested a neutralizing anti-IL-34 antibody in the suppressive MLR assay (FIG. 2A). The addition at increased concentration of blocking anti-IL-34 Ab resulted in a dose dependent increased of CD4+ proliferation up to 59% reversal of CD8+ Tregs-mediated inhibition.

Given that IL-34 has similarities with M-CSF, that we observed a significant expression of M-CSF by CD8+ CD40Ig Tregs compared to naive CD8+CD45RC$^{low}$ Tregs (FIG. 6A), and compete for the same receptor (18, 19), we wanted to address the possibility that M-CSF could play a role in the inhibition of the proliferation of effector T cells. First of all, we tested the suppressive potential of M-CSF in the MLR assay described before. Interestingly, we observed that M-CSF efficiently suppressed up in a dose dependent manner up to 93.5% of CD4+ CD25− T cells proliferation (FIG. 6B), suggesting that M-CSF-mediated suppression, as for IL-34, acts through pDCs expressing the CSF1-R (20, 21). However, the addition of a blocking anti-M-CSF Ab in co-culture suppressive assays in the presence of CD8+ Tregs did not restore CD4+ T cell proliferation, demonstrating that M-CSF was not involved in CD8+CD40Ig Treg-mediated suppression (FIG. 2B).

We next tested the involvement of CSF1-R, the only peripheral receptor described until now for IL-34 (18, 19) expressed by monocytes/macrophages, cDCs and pDCs (20, 21). Thus, we used an anti-CSF1-R-blocking Ab that has been previously shown to inhibit M-CSF actions in both rats and mice (22). We demonstrated that blocking of CSF1-R significantly abrogated CD8+ Treg-mediated suppression on CD4+ T cell proliferation in presence of pDCs (FIG. 2C).

In conclusion, we demonstrated the involvement of IL-34/CFS1-R interactions, but not M-CSF/CSF1-R interactions, in the suppressive effect of CD8+CD40Ig Tregs.

Generation of an adeno-associated viral (AAV) vector for sustained expression of IL-34: To further analyze the suppressive activity of IL-34, and since recombinant IL-34 rat cytokine was not commercially available and difficult to produce for in vivo experiments, we generated a recombinant AAV vector encoding IL-34 rat molecule, as we have done before for other molecules in primates (23) and rats (24). In this vector, the rat IL-34 cDNA was fused with a C-terminal Myc tag and both plasmid (pIIL-34) and lentivirus were first used to stably transfect or transduced HEK293 T cell lines. IL-34 expression was indicated by flow cytometry for the Myc-tag. Myc staining was not detectable on untransfected or AAV-GFP transduced HEK293 T cells, as well as on HEK293 T cells stained with isotypic control Ab. However, HEK293 T cells transfected with pIIL-34 or transduced with AAV-IL-34 expressed strong amount of IL-34 protein in a dose dependent manner, demonstrating the secretion of IL-34 and the functionality of the vector.

We then tested the suppressive potential of AAV-IL34 transduced HEK293 T cells culture supernatant (FIG. 3A) and sera of AAV-IL34 treated-rats (FIG. 3B), that both contain high amount of IL-34 protein, as shown previously. We observed that both supernatant from AAVIL-34-transduced cells and sera from AAV-IL34 treated rats significantly inhibited the proliferative response of CD4+ effector T cells stimulated by allogeneic pDCs (in a dose dependent manner) in comparison to controls (FIGS. 3A and 3B).

Altogether, these results demonstrated the functionality of the vector and the suppressive efficacy of IL-34 in inhibiting effector T cells proliferation, thus suggesting its potential in vivo in transplantation.

Therapeutic effect of IL-34 in allograft tolerance induction: To further determine the suppressive potential of IL-34 in vivo as a therapeutic strategy, we treated recipients with either AAV-IL-34 $1.10^{12}$ vg/rat or a control non-coding AAV, i.v. one month before transplantation. Such treatment with IL-34 alone resulted in a significant prolongation of allograft survival (mean survival time 32.6±7.8 days) vs. controls injected with non-coding AAV (14.2±1.8 days) or untreated recipients (7.8±0.6 days) (FIG. 4). To improve allograft survival, recipients were then treated with a suboptimal dose of rapamycin (during 14 days) in addition to the AAV vector. 14 days of rapamycin alone did not significantly extend allograft survival (FIG. 4, black circle). In contrast, we observed an indefinite allograft survival in 75% of the recipients that had received the combined therapy AAV-IL34 and rapamycine compared to controls (p<0.001, FIG. 4). Analysis of graft of long-surviving recipients for signs of chronic rejection revealed a complete absence of vascular lesions i.e. normal vessel structure and absence of leukocyte infiltration in the myocardium in all recipients analyzed. In addition, analysis of presence of anti-donor antibodies in the sera of long-surviving recipients revealed a significant inhibition of total IgG, IgG1, IgG2a and IgG2b anti-donor Abs versus recipient treated with the non coding AAV.

Altogether, we were able to demonstrate for the first time that IL-34 is a valuable therapeutic strategy for tolerance induction in combination with rapamycin and resulted in abrogation of all allogeneic immune responses.

IL-34 potently induces regulatory T cells capable of infectious tolerance: As demonstrated above, IL34 is produced specifically by CD8+CD40Ig Tregs. We next assessed whether regulatory cells were induced in the context of IL34-treatment and involved in the long-term allograft survival generated by AAV-IL34 and rapamycin combination. To do so, we performed adoptive cell transfer experiments using splenocytes of long-surviving recipients into naive grafted irradiated recipients, as we have done before (15). First adoptive transfer of $1,5.10^8$ splenocytes into secondary naive grafted irradiated recipients resulted in significant prolongation of allograft survival of 60% of the recipients (FIG. 5A), demonstrating that IL-34 efficiently induces regulatory cells. We investigated the anatomopathological status of the graft of first adoptively transferred long-term splenocytes recipients and observed a complete absence of vascular lesions and obstructions (i.e. no signs of chronic rejection). We then determined whether this prolongation of allograft survival can be serially transferred to second and third recipients and we observed that tolerance can be serially transferred at least 3 times into naive grafted irradiated recipients (FIG. 5, $2^{nd}$ and $3^{rd}$ Transfer).

Given that IL-34 was recently described to induce regulatory macrophages (25), we investigated the regulatory population allowing serial adoptive tolerance transfer including macrophages. To do so, we purified sub-populations of the different main subsets (B cells, T cells and macrophages) from tolerant recipients treated with IL34 and performed adoptive cell transfer into naive irradiated grafted recipients (FIG. 5B). To our surprise, we observed that tolerance transfer was achieved only with T-cell transfer, and not macrophages as suggested by others, demonstrating for the first time that IL-34 can induce regulatory T cells and that in our model, macrophages were not potent enough to inhibit acute allograft rejection. However, regulatory T cells do not express the IL-34' s receptor suggesting that macrophages are a necessary intermediate in regulatory T cells functions. To further determine which Treg population (i.e. $CD4^+CD25^{high}$ or $CD8^+CD45RC^{low}$ T cells) could give tolerance to newly grafted recipients, we sorted $CD4^+CD25^{high}$ and $CD8^+CD45RC^{low}$ Tregs and performed adoptive cell transfer (FIG. 5B). We observed that both adoptive transfers of $CD4^+CD25^{high}$ and $CD8^+CD45RC^{low}$ Tregs resulted in 50% of long-term allograft survival in recipients, suggesting that both populations of Tregs had been equally potentiated by the IL34-modified macrophages.

Altogether, these in vivo results demonstrate that efficient Tregs are generated following IL34-treatment in the context of reduced inflammation and transplantation, and that those Tregs can induce serial tolerance in a dominant fashion.

Treg Induction is Mediated by IL34 Modified-Macrophages Infiltrating the Graft

In an attempt to further identify the role of IL-34-induced macrophages in the induction of tolerance, we characterized the effect of IL34 on macrophages in the context of tolerance induction to an allograft. We first sorted macrophages from spleen, blood and graft of AAV-IL34 treated recipients at day 15 following transplantation (i.e. day 45 post-AAV injection) and macrophages from naive rats and analyzed by qPCR a number of genes (FIG. 7). Interestingly, we observed that macrophages in the graft from AAV-IL34-treated recipients strongly upregulated arginase 1 and inducible NO synthase (iNOS), both implicated in the metabolism of essential amino acids and described as common mechanism of immunoregulation of suppressive macrophages by limiting proliferation of T lymphocytes (34), compared to naive macrophages. We also observed an increased expression of CD14 and a decreased expression of CD23, CD86 and IL10, mostly in the graft, but also in the spleen and the blood of AAV-IL34 treated macrophages compared to naive macrophages. Finally, we observed no significant differences for CD16, CD32, ILL TGFβ and TNFα expression. It is also interesting to note that there were significant differences between macrophages located in the blood versus the graft, suggesting that IL34-modified regulatory macrophages migrate and locate in the graft quickly after transplantation. We further depleted the macrophages populations using clodronate-loaded liposomes from day −25 before transplantation to day 3 after transplantation and treated simultaneously with IL34 or non-coding AAV plus sub-optimal dose of rapamycin during 10 days, as previously described by others. Unfortunately, this therapy resulted in itself in allograft survival and could not be used to reveal the role of IL-34-induced macrophages. By doing so, AAV-IL34 injected 30 days before transplantation could not act through macrophages that were depleted at that same time. Significantly, by the time the liposome depletion started, most of the AAV serotype 8 had been integrated in the hepatocytes from the liver. We observed that recipients treated with clodronate-loaded liposomes rejected their graft more quickly after transplantation compared to the control group, demonstrating that macrophages are essential in tolerance induction by IL34 (FIG. 8).

IL34 possesses a strong suppressive potential: As we suspected a suppressive potential of IL34 in human, we added different doses of soluble human IL34 to a MLR where $CD4^+CD25^-$ CFSE-labeled effector T cells were cultured in presence of T-cell depleted allogeneic PBMCs as APCs (FIG. 9A). We observed a significant dose-dependent inhibition of effector T-cell proliferation in the presence of IL34, thus confirming the suppressive potential of IL34 on anti-donor immune response. Finally, to demonstrate the involvement of IL34 in $CD4^+CD25^{high}$ $CD127^{low}$ and $CD8^+CD45RC^{low}$ Treg-mediated suppressive activity on anti-donor immune responses, we added either anti-human IL34 blocking Ab or a control isotype Ab to a MLR where CFSE-labeled $CD4^+CD25^-$ effector T-cell proliferation in the presence of allogeneic T-depleted PBMCs is inhibited by Tregs (FIG. 9B). We observed that blocking IL34 significantly reverted Treg-mediated suppression for both $CD4^+$ and $CD8^+$ Tregs compared with isotype control Ab, demonstrating the key role of IL34 in Tregs' suppressive activity.

Altogether, these data prove the relevance of our findings and provide the proof of concept of IL34 as a Treg-specific protein and a potential therapeutic target in manipulating the anti-donor immune response.

DISCUSSION

The biological relevance of IL-34 remains to date largely unknown and controversial. The current understanding of the role of IL-34 was mostly driven by study on pathological situations were IL-34 was found to exert inflammatory functions, such as M-CSF. Various studies have shown that M-CSF administration increases inflammation in a model of collagen-induced RA (26) and that IL-34 correlates with severity of synovitis, inflammation in a model of RA (13) and can be induced by TNFα, as M-CSF (27). Furthermore, both IL-34 and M-CSF induce proinflammatory cytokines as IL-6, IP10/CXCL10, IL-8/CXCL8, MCP1/CCL2 (28). In contrast with these studies, it has also been shown that M-CSF and more recently IL-34, alone or in combination with other cytokines, can induce regulatory macrophages (25, 29-32). In transplantation, it has been demonstrated that M-CSF pre-treatment of mice expand macrophages and inhibit GVHD (33). In addition, combination of M-CSF and IFNy differentiate monocytes in regulatory macrophages capable to prolong heart allograft survival in an iNOS dependent manner (34). These studies underlie the paradoxical role of IL-34. In our study, in an attempt to unravel the complex mechanisms of tolerance induction in transplantation, we provide evidences, for the first time, of the unexpected properties of IL-34 as a master regulator of immune responses and tolerance. We also provide the first proof that IL-34 can be expressed by tolerated allografts and CD8+CD45RC$^{low}$ Tregs, and most importantly can induce potent regulatory T cells.

We previously demonstrated that treatment of cardiac graft recipients with an adenovirus encoding CD40Ig lead to indefinite allograft survival in 93% of the recipients, and that this acceptance was mediated by CD8+CD45RC$^{low}$ Treg in a IFNγ, IDO and FGL2 dependent manner. We more recently demonstrated that CD8+CD45RC$^{low}$ Treg recombined a biased restricted Vβ11 repertoire to recognize a dominant MCH class II derived peptide, and that this peptide induces regulatory Tregs and induces tolerance (17). In the present specification, we show that IL-34 was expressed at high level by tolerated grafts of AdCD40Ig—treated recipients, and importantly, also by splenic CD8+CD45RC$^{low}$ Tregs from the same recipients. Furthermore, CD8+CD45RC$^{low}$ Tregs mediated suppression can be partially abrogated by blockade of IL-34. Thus, IL-34 possesses immunosuppressive properties that have never been studied until now, and acts in synergy with FGL2, IDO and IFNγ in the CD40Ig model of suppression mediated by CD8+CD45RC$^{low}$ Tregs (16).

We also demonstrated that this property was specific of IL-34 since we observed that M-CSF was not involved in this model. Accumulating evidences suggest that IL-34 and M-CSF exhibit specific and non-redundant properties. This is underlined by structural analysis comparison showing that IL-34 and M-CSF bind differently to CD115 (11, 19). The identification more recently of a second distinct receptor for IL-34 reinforces this interpretation (10). Very recently, IL-34-deficient mice have been generated and showed disappearance of certain cell subsets such as Langerhan's cells and microglia (12), effects that had not been observed in M-CSF KO mice and demonstrating, not only a different temporal and spatial expression role, but also different functional effects for IL-34 vs. M-CSF.

The therapeutic value of this molecule was evidenced with the generation of an AAV encoding IL-34. With this vector, we were able to show for the first time the potent immunosuppressive properties of IL-34 in vitro and, most importantly in vivo where we obtained indefinite allograft survival in 80% of the recipients when combined with a sub-optimal dose of rapamycin. We also demonstrated that such therapy resulted in abrogation of all allogeneic immune responses and the induction of tolerance. Previous studies demonstrated that both M-CSF and IL-34 can differentiate monocytes in regulatory macrophages (25, 34) and the regulatory macrophages induced in vitro by M-CSF and IFNy can be used in vivo to prolong heart allograft survival in mice (34). Another study demonstrated in mice that administration of M-CSF before transplant can expand macrophages and thus limit donor T cell expansion and GVHD (33). Chen et al. showed in mice treated with soluble IL-34 protein an increase of the CD11b+ population (35). Moreover, other studies noticed a decrease in pDC and cDC in CSF-1-deficient osteopetrotic mice (21), and a CFS1-induced increase in DC number (20). Surprisingly, and in contrast with other study, in vivo IL-34 tolerogenic effect following administration was mediated by regulatory T cells. Indeed, we demonstrated that the tolerance obtained in AAV-IL-34-treated recipients could be transferred in newly grafted irradiated recipients for at least 3 generations and that this effect was mediated by Tregs, but, despite the increase observed for the CD11b+ cell population, not by macrophages. However, since Tregs do not express IL-34's receptor, we can hypothesize that IL-34 mediated its effect on Tregs through macrophages as it has been shown in the literature that regulatory macrophages can anergizing CD4 effector T cells (36), converting T cells in Tregs (37) or inhibiting other APCs presentation (38). We could not conclude that IL-34 induces regulatory macrophages in our model, but these are necessary intermediate in IL-34 induced Tregs. These results highlight the functional differences of IL-34 and M-CSF and the controversy on this topic as several studies showed the pro-inflammatory role of MCSF that increases macrophage proliferation and accumulation in rejected renal allograft (39).

In conclusion, we described here the role in transplantation tolerance of a new cytokine, IL-34, and we revealed its potential as a therapy in transplantation or as a biomarker associated with better prognosis in transplantation, but also by extension in other diseases. We also demonstrated for the first time that this cytokine can be produced by CD8+ Tregs and can in turn, induce Tregs capable of tolerance induction in a dominant manner, opening new possibilities in the generation of Tregs transferrable to the human setting.

REFERENCES

Throughout this application, various references describe the state of the art to which this invention pertains. The disclosures of these references are hereby incorporated by reference into the present disclosure.
1. Nankivell B J, et al. (2003) The natural history of chronic allograft nephropathy. *N Engl J Med* 349(24):2326-2333.
2. Srinivas T R & Kaplan B (2012) Transplantation in 2011: New agents, new ideas and new hope. *Nat Rev Nephrol* 8(2):74-75.
3. Londono M C, et al. (2012) A need for biomarkers of operational tolerance in liver and kidney transplantation. *Am J Transplant* 12(6):1370-1377.
4. Wood K J, Bushell A, & Hester J (2012) Regulatory immune cells in transplantation. *Nat Rev Immunol* 12(6): 417-430.
5. Niederkorn J Y (2008) Emerging concepts in CD8(+) T regulatory cells. *Curr Opin Immunol* 20(3):327-331.
6. Picarda E, Anegon I, & Guillonneau C (2011) T-cell receptor specificity of CD8(+) Tregs in allotransplantation. *Immunotherapy* 3(4 Suppl):35-37.
7. Guillonneau C, Picarda E, & Anegon I (2010) CD8+ regulatory T cells in solid organ transplantation. *Curr Opin Organ Transplant* 15(6):751-756.
8. Menoret S, et al. (2011) Phenotypic and functional characterization of CD8(+) T regulatory cells. *Methods Mol Biol* 677:63-83.
9. Wei S, et al. (2010) Functional overlap but differential expression of CSF-1 and IL-34 in their CSF-1 receptor-mediated regulation of myeloid cells. *J Leukoc Biol* 88(3):495-505.
10. Nandi S, et al. (2013) Receptor-type protein-tyrosine phosphatase zeta is a functional receptor for interleukin-34. *J Biol Chem* 288(30):21972-21986.
11. Chihara T, et al. (2010) IL-34 and M-CSF share the receptor Fms but are not identical in biological activity and signal activation. *Cell Death Differ* 17(12):1917-1927.
12. Wang Y, et al. (2012) IL-34 is a tissue-restricted ligand of CSF1R required for the development of Langerhans cells and microglia. *Nat Immunol* 13(8):753-760.
13. Chemel M, et al. (2012) Interleukin 34 expression is associated with synovitis severity in rheumatoid arthritis patients. *Ann Rheum Dis* 71(1):150-154.

14. Baud'huin M, et al. (2010) Interleukin-34 is expressed by giant cell tumours of bone and plays a key role in RANKL-induced osteoclastogenesis. *J Pathol* 221(1):77-86.
15. Guillonneau C, et al. (2007) CD40Ig treatment results in allograft acceptance mediated by CD8CD45RC T cells, IFN-gamma, and indoleamine 2,3-dioxygenase. *J Clin Invest* 117(4):1096-1106.
16. Li X L, et al. (2010) Mechanism and localization of CD8 regulatory T cells in a heart transplant model of tolerance. *J Immunol* 185(2):823-833.
17. Picarda E, et al. (2014) MHC-derived allopeptide activates TCR-biased CD8+Tregs and suppresses organ rejection. *J Clin Invest.*
18. Lin H, et al. (2008) Discovery of a cytokine and its receptor by functional screening of the extracellular proteome. *Science* 320(5877):807-811.
19. Garceau V, et al. (2010) Pivotal Advance: Avian colony-stimulating factor 1 (CSF-1), interleukin-34 (IL-34), and CSF-1 receptor genes and gene products. *J Leukoc Biol* 87(5):753-764.
20. Fancke B, Suter M, Hochrein H, & O'Keeffe M (2008) M-CSF: a novel plasmacytoid and conventional dendritic cell poietin. *Blood* 111(1):150-159.
21. MacDonald K P, et al. (2005) The colony-stimulating factor 1 receptor is expressed on dendritic cells during differentiation and regulates their expansion. *J Immunol* 175(3):1399-1405.
22. Gilmore G L & Shadduck R K (1995) Inhibition of day-12 spleen colony-forming units by a monoclonal antibody to the murine macrophage/monocyte colony-stimulating factor receptor. *Blood* 85(10):2731-2734.
23. Toromanoff A, et al. (2008) Safety and efficacy of regional intravenous (r.i.) versus intramuscular (i.m.) delivery of rAAV1 and rAAV8 to nonhuman primate skeletal muscle. *Mol Ther* 16(7):1291-1299.
24. Le Texier L, et al. (2012) Immunoregulatory function of IL-27 and TGF-beta1 in cardiac allograft transplantation. *Transplantation* 94(3):226-233.
25. Foucher ED, et al. (2013) IL-34 induces the differentiation of human monocytes into immunosuppressive macrophages. antagonistic effects of GM-CSF and IFN-gamma. *PLoS One* 8(2):e56045.
26. Campbell I K, Rich M J, Bischof R J, & Hamilton J A (2000) The colony-stimulating factors and collagen-induced arthritis: exacerbation of disease by M-CSF and G-CSF and requirement for endogenous M-CSF. *J Leukoc Biol* 68(1):144-150.
27. Hamilton J A (2008) Colony-stimulating factors in inflammation and autoimmunity. *Nat Rev Immunol* 8(7): 533-544.
28. Eda H, et al. (2010) Macrophage-colony stimulating factor and interleukin-34 induce chemokines in human whole blood. *Cytokine* 52(3):215-220.
29. Doyle A G, Halliday W J, Barnett C J, Dunn T L, & Hume D A (1992) Effect of recombinant human macrophage colony-stimulating factor 1 on immunopathology of experimental brucellosis in mice. *Infect Immun* 60(4): 1465-1472.
30. Sakurai T, Wakimoto N, Yamada M, Shimamura S, & Motoyoshi K (1998) Effect of macrophage colony-stimulating factor (M-CSF) on mouse immune responses in vivo. *Immunopharmacol Immunotoxicol* 20(1):79-102.
31. Sakurai T, Yamada M, Simamura S, & Motoyoshi K (1996) Recombinant human macrophage-colony stimulating factor suppresses the mouse mixed lymphocyte reaction. *Cell Immunol* 171(1):87-94.
32. Duluc D, et al. (2007) Tumor-associated leukemia inhibitory factor and IL-6 skew monocyte differentiation into tumor-associated macrophage-like cells. *Blood* 110 (13):4319-4330.
33. Hashimoto D, et al. (2011) Pretransplant CSF-1 therapy expands recipient macrophages and ameliorates GVHD after allogeneic hematopoietic cell transplantation. *J Exp Med* 208(5):1069-1082.
34. Riquelme P, et al. (2013) IFN-gamma-induced iNOS expression in mouse regulatory macrophages prolongs allograft survival in fully immunocompetent recipients. *Mol Ther* 21(2):409-422.
35. Chen Z, Buki K, Vaaraniemi J, Gu G, & Vaananen HK (2011) The critical role of IL-34 in osteoclastogenesis. *PLoS One* 6(4):e18689.
36. Tzachanis D, Berezovskaya A, Nadler L M, & Boussiotis V A (2002) Blockade of B7/CD28 in mixed lymphocyte reaction cultures results in the generation of alternatively activated macrophages, which suppress T-cell responses. *Blood* 99(4):1465-1473.
37. Liu G, et al. (2011) An instructive role of donor macrophages in mixed chimeras in the induction of recipient CD4(+)Foxp3(+) Treg cells. *Immunol Cell Biol* 89(8): 827-835.
38. Holt P G, Schon-Hegrad M A, & Oliver J (1988) MHC class II antigen-bearing dendritic cells in pulmonary tissues of the rat. Regulation of antigen presentation activity by endogenous macrophage populations. *J Exp Med* 167 (2):262-274.
39. Jose M D, Le Meur Y, Atkins R C, & Chadban S J (2003) Blockade of macrophage colony-stimulating factor reduces macrophage proliferation and accumulation in renal allograft rejection. *Am J Transplant* 3(3):294-300.
40. Ma X, Lin W Y, Chen Y, Stawicki S, Mukhyala K, Wu Y, Martin F, Bazan J F, Starovasnik (2012) MA Structural basis for the dual recognition of helical cytokines IL-34 and CSF-1 by CSF-1R. *Structure* April 4; 20(4):676-87.
41. Van Rooijen, N., and Sanders, A. 1994. Liposome mediated depletion of macrophages: mechanism of action, preparation of liposomes and applications. *J Immunol Methods* 174:83-93.
42. Jain N K, Mishra V, Mehra N K. Targeted drug delivery to macrophages. *Expert Opin Drug Deliv.* 2013 March; 10(3):353-67.

The invention claimed is:

1. A method of treating an autoimmune disease, wherein said autoimmune disease involves CD4+ and/or CD8+ T cells, an unwanted immune response against a therapeutic protein or an allergy in a subject in need thereof, comprising administering an effective amount of interleukin-34 (IL-34) to said subject.

2. The method according to claim 1, wherein IL-34 is administered to the subject in the form of an IL-34 polypeptide.

3. The method according to claim 2, wherein the IL-34 polypeptide has an amino acid sequence sharing at least 80% of sequence identity with the amino acid sequence of SEQ ID NO: 1 while maintaining its ability to inhibit CD4+ and CD8+ T cell proliferation in a mixed lymphocyte reaction (MLR).

4. The method according to claim 2, wherein the IL-34 polypeptide has an amino acid sequence sharing at least 80% of sequence identity with the amino acid sequence of SEQ ID NO: 1 while maintaining its ability to inhibit CD4+ and CD8+ T cell proliferation in a mixed lymphocyte reaction (MLR), and wherein the IL-34 polypeptide comprises one of an E123Q substitution, a S195T substitution, and a Q81 deletion.

5. The method according to claim 2, wherein the IL-34 polypeptide is a full-length human IL-34 polypeptide with an amino acid sequence of SEQ ID NO: 1.

6. The method according to claim 1, wherein the autoimmune disease is selected from the group consisting of rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease, autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosus, autoimmune thrombocytopenia purpura, Goodpasture's syndrome, Addison's disease, systemic sclerosis, polymyositis, dermatomyositis, acquired hemophilia, and thrombotic thrombocytopenic purpura.

7. The method according to claim 1, wherein the autoimmune disease is inflammatory bowel disease.

8. The method according to claim 7, wherein inflammatory bowel disease is one of Crohn's disease and ulcerative colitis.

9. The method according to claim 1, wherein the autoimmune disease is multiple sclerosis.

10. The method of claim 1, wherein the therapeutic protein is selected from the group consisting of antibodies, cytokines, enzymes, and coagulation factors.

11. The method of claim 1, wherein the allergy is selected from the group consisting of include eczema, hives, hay fever, asthma, food allergies, and reactions to venom of stinging insects.

* * * * *

SEQUENCE LISTING

<160> NUMBER OF SEQ ID NOS: 7

<210> SEQ ID NO 1
<211> LENGTH: 242
<212> TYPE: PRT
<213> ORGANISM: Homo sapiens

<400> SEQUENCE: 1

```
Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
            100                 105                 110

His Pro Ser Trp Lys Tyr Leu Gln Glu Val Glu Thr Leu Leu Leu Asn
        115                 120                 125

Val Gln Gln Gly Leu Thr Asp Val Glu Val Ser Pro Lys Val Glu Ser
130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190

Val Pro Ser Pro Gln Ser Cys Ser Pro Glu Pro Ser Leu Gln Tyr Ala
        195                 200                 205

Ala Thr Gln Leu Tyr Pro Pro Pro Trp Ser Pro Ser Ser Pro Pro Pro
210                 215                 220

His Ser Thr Gly Ser Val Arg Pro Val Arg Ala Gln Gly Glu Gly Leu
225                 230                 235                 240

Leu Pro
```

<210> SEQ ID NO 2
<211> LENGTH: 20
<212> TYPE: DNA
<213> ORGANISM: Artificial
<220> FEATURE:
<223> OTHER INFORMATION: Synthetic Forward primer IL-34 quantitative
      RT-PCR

<400> SEQUENCE: 2
ctggctgtcc tctaccctga                                              20

<210> SEQ ID NO 3
<211> LENGTH: 21
<212> TYPE: DNA
<213> ORGANISM: Artificial
<220> FEATURE:
<223> OTHER INFORMATION: Synthetic Reverse primer IL-34 quantitative
      RT-PCR

<400> SEQUENCE: 3
tgtcgtggca agatatggca a                                            21

<210> SEQ ID NO 4
<211> LENGTH: 256
<212> TYPE: PRT

<213> ORGANISM: Homo sapiens

<400> SEQUENCE: 4

```
Met Thr Ala Pro Gly Ala Ala Gly Arg Cys Pro Pro Thr Thr Trp Leu
1               5                   10                  15
Gly Ser Leu Leu Leu Leu Val Cys Leu Leu Ala Ser Arg Ser Ile Thr
            20                  25                  30
Glu Glu Val Ser Glu Tyr Cys Ser His Met Ile Gly Ser Gly His Leu
        35                  40                  45
Gln Ser Leu Gln Arg Leu Ile Asp Ser Gln Met Glu Thr Ser Cys Gln
    50                  55                  60
Ile Thr Phe Glu Phe Val Asp Gln Glu Gln Leu Lys Asp Pro Val Cys
65                  70                  75                  80
Tyr Leu Lys Lys Ala Phe Leu Leu Val Gln Asp Ile Met Glu Asp Thr
                85                  90                  95
Met Arg Phe Arg Asp Asn Thr Pro Asn Ala Ile Ala Ile Val Gln Leu
            100                 105                 110
Gln Glu Leu Ser Leu Arg Leu Lys Ser Cys Phe Thr Lys Asp Tyr Glu
        115                 120                 125
Glu His Asp Lys Ala Cys Val Arg Thr Phe Tyr Glu Thr Pro Leu Gln
    130                 135                 140
Leu Leu Glu Lys Val Lys Asn Val Phe Asn Glu Thr Lys Asn Leu Leu
145                 150                 155                 160
Asp Lys Asp Trp Asn Ile Phe Ser Lys Asn Cys Asn Asn Ser Phe Ala
                165                 170                 175
Glu Cys Ser Ser Gln Gly His Glu Arg Gln Ser Glu Gly Ser Phe Ser
            180                 185                 190
Pro Gln Leu Gln Glu Ser Val Phe His Leu Leu Val Pro Ser Val Ile
        195                 200                 205
Leu Val Leu Leu Ala Val Gly Gly Leu Leu Phe Tyr Arg Trp Arg Arg
    210                 215                 220
Arg Ser His Gln Glu Pro Gln Arg Ala Asp Ser Pro Leu Glu Gln Pro
225                 230                 235                 240
Glu Gly Ser Pro Leu Thr Gln Asp Asp Arg Gln Val Glu Leu Pro Val
                245                 250                 255
```

<210> SEQ ID NO 5
<211> LENGTH: 554
<212> TYPE: PRT
<213> ORGANISM: Homo sapiens

<400> SEQUENCE: 5

```
Met Thr Ala Pro Gly Ala Ala Gly Arg Cys Pro Pro Thr Thr Trp Leu
1               5                   10                  15
Gly Ser Leu Leu Leu Leu Val Cys Leu Leu Ala Ser Arg Ser Ile Thr
            20                  25                  30
Glu Glu Val Ser Glu Tyr Cys Ser His Met Ile Gly Ser Gly His Leu
        35                  40                  45
Gln Ser Leu Gln Arg Leu Ile Asp Ser Gln Met Glu Thr Ser Cys Gln
    50                  55                  60
Ile Thr Phe Glu Phe Val Asp Gln Glu Gln Leu Lys Asp Pro Val Cys
65                  70                  75                  80
Tyr Leu Lys Lys Ala Phe Leu Leu Val Gln Asp Ile Met Glu Asp Thr
                85                  90                  95
Met Arg Phe Arg Asp Asn Thr Pro Asn Ala Ile Ala Ile Val Gln Leu
```

-continued

```
                100             105             110
    Gln Glu Leu Ser Leu Arg Leu Lys Ser Cys Phe Thr Lys Asp Tyr Glu
            115                 120                 125

Glu His Asp Lys Ala Cys Val Arg Thr Phe Tyr Glu Thr Pro Leu Gln
            130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                    165                 170                 175

Glu Cys Ser Ser Gln Asp Val Val Thr Lys Pro Asp Cys Asn Cys Leu
                180                 185                 190

Tyr Pro Lys Ala Ile Pro Ser Ser Asp Pro Ala Ser Val Ser Pro His
            195                 200                 205

Gln Pro Leu Ala Pro Ser Met Ala Pro Val Ala Gly Leu Thr Trp Glu
        210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                    245                 250                 255

Thr Cys Gln Ser Phe Glu Pro Pro Glu Thr Pro Val Val Lys Asp Ser
                260                 265                 270

Thr Ile Gly Gly Ser Pro Gln Pro Arg Pro Ser Val Gly Ala Phe Asn
            275                 280                 285

Pro Gly Met Glu Asp Ile Leu Asp Ser Ala Met Gly Thr Asn Trp Val
        290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Ser Met Gln Thr Glu
                    325                 330                 335

Pro Ala Arg Pro Ser Asn Phe Leu Ser Ala Ser Ser Pro Leu Pro Ala
                340                 345                 350

Ser Ala Lys Gly Gln Gln Pro Ala Asp Val Thr Gly Thr Ala Leu Pro
            355                 360                 365

Arg Val Gly Pro Val Arg Pro Thr Gly Gln Asp Trp Asn His Thr Pro
        370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
                    405                 410                 415

Ser Thr Leu Ser Ala Gln Pro Gln Leu Ser Arg Ser His Ser Ser Gly
                420                 425                 430

Ser Val Leu Pro Leu Gly Glu Leu Gly Arg Arg Ser Thr Arg Asp
            435                 440                 445

Arg Arg Ser Pro Ala Glu Pro Glu Gly Gly Pro Ala Ser Glu Gly Ala
        450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Ser Pro Gln Leu Gln Glu Ser
                    485                 490                 495

Val Phe His Leu Leu Val Pro Ser Val Ile Leu Val Leu Leu Ala Val
                500                 505                 510

Gly Gly Leu Leu Phe Tyr Arg Trp Arg Arg Ser His Gln Glu Pro
            515                 520                 525
```

Gln Arg Ala Asp Ser Pro Leu Glu Gln Pro Glu Gly Ser Pro Leu Thr
    530                 535                 540

Gln Asp Asp Arg Gln Val Glu Leu Pro Val
545                 550

<210> SEQ ID NO 6
<211> LENGTH: 438
<212> TYPE: PRT
<213> ORGANISM: Homo sapiens

<400> SEQUENCE: 6

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
        275                 280                 285

Pro Gly Met Glu Asp Ile Leu Asp Ser Ala Met Gly Thr Asn Trp Val
    290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala

```
                    340                 345                 350
Ser Ala Lys Gly Gln Gln Pro Ala Asp Val Thr Gly His Glu Arg Gln
            355                 360                 365

Ser Glu Gly Ser Ser Ser Pro Gln Leu Gln Glu Ser Val Phe His Leu
            370                 375                 380

Leu Val Pro Ser Val Ile Leu Val Leu Leu Ala Val Gly Gly Leu Leu
385                 390                 395                 400

Phe Tyr Arg Trp Arg Arg Arg Ser His Gln Glu Pro Gln Arg Ala Asp
                405                 410                 415

Ser Pro Leu Glu Gln Pro Glu Gly Ser Pro Leu Thr Gln Asp Asp Arg
            420                 425                 430

Gln Val Glu Leu Pro Val
            435

<210> SEQ ID NO 7
<211> LENGTH: 150
<212> TYPE: PRT
<213> ORGANISM: Artificial
<220> FEATURE:
<223> OTHER INFORMATION: Synthetic Recombinant human M-CSF fragment of
      150 amino acids

<400> SEQUENCE: 7

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys
145                 150
```